United States Patent
Vidhani et al.

(10) Patent No.: US 9,758,499 B2
(45) Date of Patent: Sep. 12, 2017

(54) STEREO CONTROLLED SYNTHESIS OF (E,Z)-DIENALS VIA TANDEM RH(I) CATALYZED PROPARGYL CLAISEN REARRANGEMENT

(71) Applicant: The Florida State University Research Foundation, Inc., Tallahassee, FL (US)

(72) Inventors: Dinesh V. Vidhani, Tallahassee, FL (US); Marie E. Krafft, Tallahassee, FL (US); Igor Alabugin, Tallahassee, FL (US)

(73) Assignee: The Florida State University Research Foundation, Inc., Tallahessee, FL (US)

( * ) Notice: Subject to any disclaimer, the term of this patent is extended or adjusted under 35 U.S.C. 154(b) by 0 days.

(21) Appl. No.: 15/398,094

(22) Filed: Jan. 4, 2017

(65) Prior Publication Data
US 2017/0129865 A1     May 11, 2017

Related U.S. Application Data

(62) Division of application No. 14/724,016, filed on May 28, 2015, now Pat. No. 9,573,871.

(60) Provisional application No. 62/011,251, filed on Jun. 12, 2014.

(51) Int. Cl.
| | |
|---|---|
| C07D 307/46 | (2006.01) |
| C07C 41/08 | (2006.01) |
| C07C 45/51 | (2006.01) |
| C07C 253/30 | (2006.01) |
| C07D 307/42 | (2006.01) |

(52) U.S. Cl.
CPC ............ *C07D 307/46* (2013.01); *C07C 41/08* (2013.01); *C07C 45/513* (2013.01); *C07C 253/30* (2013.01); *C07D 307/42* (2013.01)

(58) Field of Classification Search
CPC .............................. C07D 307/46; C07C 41/08
See application file for complete search history.

(56) References Cited

U.S. PATENT DOCUMENTS

| | | |
|---|---|---|
| 8,410,303 B2 | 4/2013 | Alabugin et al. |
| 8,927,728 B2 | 1/2015 | Alabugin et al. |
| 8,927,778 B2 | 1/2015 | Alabugin et al. |
| 9,206,100 B2 | 12/2015 | Alabugin et al. |
| 9,273,023 B2 | 3/2016 | Alabugin et al. |
| 9,573,871 B2 * | 2/2017 | Vidhani ................ C07C 45/513 |
| 2013/0196985 A1 | 8/2013 | Ding et al. |

FOREIGN PATENT DOCUMENTS

WO    2012037062 A3    3/2012

OTHER PUBLICATIONS

Vidhani, Dinesh V. et al., "Stereocontrolled Synthesis of (E,Z)-Dienals via Tandem Rh(I)-Catalyzed Rearrangement of Propargyl Vinyl Ethers", Organic Letters, 2013, pp. 4462-4465, vol. 15, No. 17, American Chemical Society.
Vidhani, Dinesh V. et al., STN International, HCAPLUS database (Columbus, Ohio), Accession No. 2013; 1316846.
Mallory, Frank B. et al., Phenacenes: a family of graphite ribbons. Part 3: Iterative strategies for the synthesis of large phenacenes, Tetrahedron, 57, © 2001 Elsevier Science Ltd., (2001) pp. 3715-3724.
Wu, Jishan et al., Graphenes as Potential Material for Electronics, Chemical Reviews, vol. 107, No. 3, © 2007 American Chemical Society, (2007), pp. 718-747.
Berresheim, Alexander J. et al., Polyphenylene Nanostructures, Chemical Reviews, vol. 99, No. 7, © 1999 American Chemical Society, (1999), pp. 1747-1785.
Geim, A.K. et al., The Rise of Graphene, Nature Materials, vol. 6, © 2007 Nature Publishing Group, (Mar. 2007), pp. 183-191.
Kuninobu, Yoichiro et al., Synthesis of Functionalized Pentacenes from Isobenzofurans Derived from C—H Bond Activation, Organic Letters, vol. 12, No. 22, © 2010 American Chemical Society, (Oct. 20, 2010), pp. 5287-5289.
Scherf, Ullrich, Ladder-type materials, J. Mater. Chem., vol. 9, 1999, pp. 1853-1864.

(Continued)

*Primary Examiner* — Golam M M Shameem
(74) *Attorney, Agent, or Firm* — Armstrong Teasdale LLP

(57) ABSTRACT

A novel Rh(I)-catalyzed approach to synthesizing functionalized (E,Z) dienal compounds has been developed via tandem transformation where a stereoselective hydrogen transfer follows a propargyl Claisen rearrangement. Z-Stereochemistry of the first double bond suggests the involvement of a six-membered cyclic intermediate whereas the E-stereochemistry of the second double bond stems from the subsequent protodemetallation step giving an (E,Z)-dienal. The reaction may be represented by the following sequence.

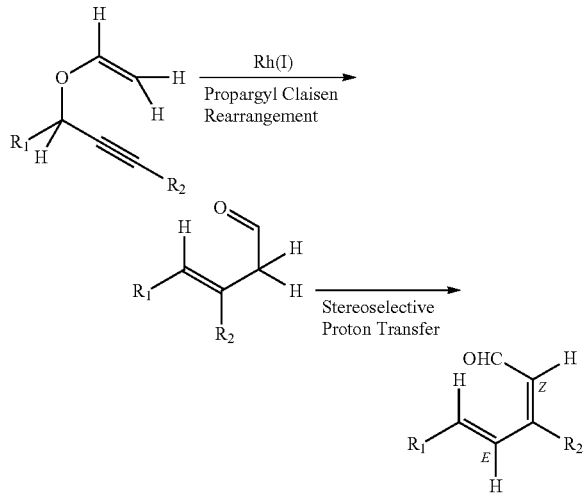

8 Claims, 3 Drawing Sheets

(56) References Cited

OTHER PUBLICATIONS

Allen, Matthew J. et al., Honeycomb Carbon: A Review of Graphene, Chemical Reviews, vol. 110, No. 1, © 2010 American Chemical Society, (Jul. 17, 2009), pp. 132-145.

Goldfinger, Marc B. et al., Fused Polycyclic Aromatics via Electrophile-Induced Cyclization Reactions: Application to the Synthesis of Graphite Ribbons, J. Am. Chem. Soc., vol. 116, No. 17, © 1994 American Chemical Society, (1994), pp. 7895-7896.

Swartz, Christopher R. et al., Synthesis and Characterization of Electron-Deficient Pentacenes, Organic Letters, vol. 7, No. 15, © 2005 American Chemical Society, (Jun. 30, 2005), pp. 3163-3166.

Li, Xiaolin et al., Chemically Derived, Ultrasmooth Graphene Nanoribbon Semiconductors, Science, vol. 319, © 2008 by the American Association for the Advancement of Science, (Feb. 29, 2008), pp. 1229-1232.

Paquette, Lee et al., The Square Ester—Polyquinane Connection. An Analysis of the Capacity of Achiral Divinyl Adducts to Rearrange Spontaneously to Polycyclic Networks Housing Multiple Sterogenic Centers, J. American Chemical Society, 1997, vol. 119, pp. 1230-1241.

Pollart, Daniel J. et al., Generation of (Trimethylsiloxy)(phenylethynyl)ketene and (Trimethylsiloxy)cyanoketene and Their Reactions with Some Alkynes, Journal of Org. Chemical, 1989, vol. 54, pp. 5444-5448.

Arns, Steve et al., Cascading pericyclic reactions: building complex carbon frameworks for natural product synthesis, Chem. Commun., 2007, pp. 2211-2221, The Royal Society of Chemistry.

Baldwin, Jack E. et al., Rules for Ring Closure: Application to Intramolecular Aldol Condensations in Polyketonic Substrates, Tetrahedron, 1982, pp. 2939-2947, vol. 38, No. 19, Great Britain.

Butenschon, Holger, Arene chromium complexes with functionalized anellated rings. Selective formation of highly substituted polycycles, Pure Appl. Chem., 2002, pp. 57-62; vol. 74, No. 1, IUPAC.

Carpenter, Barry K., A Simple Model for Predicting the Effect of Substituents on the Rates of Thermal Pericyclic Reactions, Tetrahedron, 1978, pp. 1877-1884, vol. 34, Pergamon Press Ltd.

Dahnke, Karl R. et al., Exploratory Synthetic Studies Involving the Tricyclo[9.3.0.0^2,8]tetradecane Ring System Peculiar to the Cyathins, J. Org. Chem., 1994, pp. 885-899, vol. 59, American Chemical Society.

Gentric, Lionel et al., Rate Acceleration of Anionic Oxy-Cope Rearrangements Induced by an Additional Unsaturation, Organic Letters, 2003, pp. 3631-3634, vol. 5, No. 20, American Chemical Society.

Graulich, Nicole et al., Heuristic thinking makes a chemist smart, Chemical Society Reviews, 2010, pp. 1503-1512, vol. 39, The Royal Society of Chemistry.

Huntsman, William D. et al., The Thermal Rearrangement of 1,5-Hexadiyne and Related Compounds, J. Org. Chem., Jan. 18, 1967, pp. 342-347, vol. 89, No. 2, Journal of the American Chemical Society.

Evans, D.A. et al., [3,3] Sigmatropic Rearrangements of 1,5-Diene Alkoxides. The Powerful Accelerating Effects of the Alkoxide Substituent, Journal of the American Chemical Society, Aug. 6, 1975, pp. 4765-4766, vol. 97, No. 16, American Chemical Society.

Evans, D.A. et al., A General Approach to the Synthesis of 1,6 Dicarbonyl Substrates. New Applications of Base-Accelerated Oxy-Cope Rearrangements, Journal of the American Chemical Society, Mar. 29, 1978, pp. 2242-2244, vol. 100, No. 7, American Chemical Society.

Jacobi, Peter A. et al., Bis Heteroannulation. 7. Total Syntheses of (+)-Chididione and (+)-Isognididione, J. Am. Chem. Soc., 1987, pp. 3041-3043, vol. 106, Amerian Chemical Society.

Paquette, Leo A., Recent Applications of Anionic Oxy-Cope Rearrangements, Tetrahedron Report No. 429, 1997, pp. 13971-14020, vol. 52, No. 41, Elsevier Science Ltd, Great Britian.

Roth, Wolfgang R. et al., A "Frustrated" Cope Rearrangement: Thermal Interconversion of 2,6-Diphenylhepta-1,6-diene and 1,5-Diphenylbicyclo[3.2.0]heptain, Journal of the American Chemical Society, 1990, pp. 1722-1732, vol. 112, American Chemical Society.

Pal, Runa et al., Fast Oxy-Cope Rearrangements of Bis-alkynes: Competition with Central C—C Bond Fragmentation and Incorporation in Tunable Cascades Diverging from a Common Bis-allenic Intermediate, JOC Note, 2010, pp. 3689-8692, vol. 75, J. Org. Chem.

Zimmerman, Howard E., Kinetic Protonation of Enols, Enolates, and Analogues. The Stereochemistry of Ketonization, Acc. Chem. Res., 1987, pp. 263-268, vol. 20, American Chemical Society.

Zimmerman, Howard E. et al, The Stereochemistry of Allenic Enol Tautomerism—Independent Generation and Reactivity of he Enolates, Eur. J. Org. Chem., 2006, pp. 3491-3497, Wiley-VCH Verlag GmbH & Co.

Pati, Kamalkishore, et al., Exo-Dig Radical Cascades of Skipped Enediynes: Building a Naphthalene Moiety within a Polycyclic Framework, Chemistry, A European Journal, 2014, vol. 20, pp. 390-393.

\* cited by examiner

STEREO CONTROLLED SYNTHESIS OF (E,Z)-DIENALS VIA TANDEM RH(I) CATALYZED PROPARGYL CLAISEN REARRANGEMENT

CROSS REFERENCE TO RELATED APPLICATION(S)

This application is a divisional application of U.S. application Ser. No. 14/724,016, which was filed May 28, 2015, the disclosure of which is hereby incorporated by reference as if set forth in its entirety. U.S. application Ser. No. 14/724,016 claims priority from U.S. provisional Application No. 62/011,251, filed Jun. 12, 2014, the disclosure of which is hereby incorporated by reference as if set forth in its entirety.

STATEMENT REGARDING FEDERALLY SPONSORED RESEARCH OR DEVELOPMENT

This invention was made with Government support under Grant CHE-1152491 awarded by the National Science Foundation. The Government has certain rights in the invention.

FIELD OF THE INVENTION

The present invention generally relates to a method for synthesizing functionalized (E,Z)-dienal compounds. More specifically, functionalized (E,Z)-dienal compounds are prepared by tandem transformation where a stereoselective hydrogen transfer follows a propargyl Claisen rearrangement.

BACKGROUND OF THE INVENTION

Polyene motifs with (E,Z) stereochemistry are ubiquitous in biologically active and naturally occurring systems. See (a) McGarvey, B. D.; Attygalle, A. B.; Starratt, A. N.; Xiang, B.; Schroeder, F. C.; Brandle, J. E.; Meinwald, *J. Nat. Prod.* 2003, 66,1395. (b) Robinson, C. Y.; Waterhous, D. V.; Muccio, D. D.; Brouillette, W. J. *Bioorg. Med. Chem. Lett.*, 1995, 5, 953. (c) Asfaw, N.; Storesund, H. J.; Skattebol, L.; Aasen A, J. *Phytochemistry* 1999, 52, 1491. (d) Hiraoka, H.; Mori, N.; Nishida, R.; Kuwahara, Y. *Biosci. Biotechnol. Biochem.,* 2001, 65, 2749. (e) Matsumoto, H.; Asato, A. E.; Denny, M.; Baretz, B.; Yen, Y-P.; Tong, D.; Liu, R. S. H. *Biochemistry,* 1980, 19, 4589. Several natural compounds are shown below:

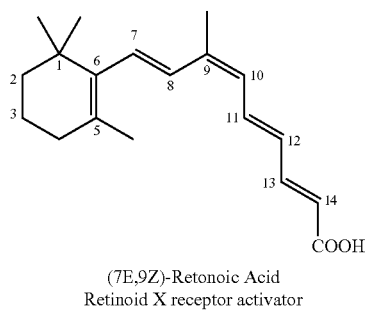

(7E,9Z)-Retonoic Acid
Retinoid X receptor activator

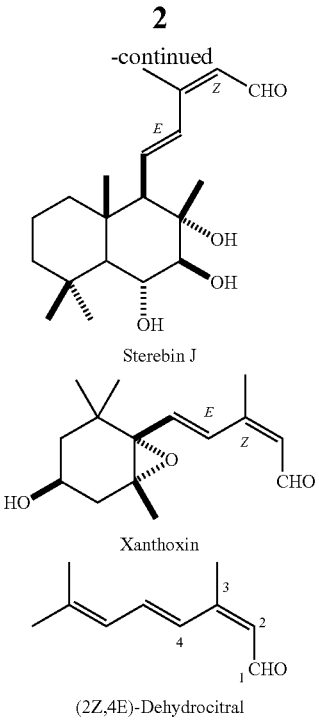

Sterebin J

Xanthoxin (2Z,4E)-Dehydrocitral

Accordingly, polyene motifs with (E, Z) stereochemistry represent synthetically important targets. See (a) Knowles, W. S. *Angew. Chem., Int. Ed.* 2002, 41, 1998. Noyori, R. *Angew. Chem., Int. Ed.* 2002, 41, 2008. (b) Sharpless, K. B. *Angew. Chem., Int. Ed.* 2002, 41, 2024. (c) Chauvin, Y. *Angew. Chem., Int. Ed.* 2006, 45, 3740. (d) Schrock, R. R. *Angew. Chem., Int. Ed.* 2006, 45, 374. (e) Grubbs, R. H. *Angew. Chem., Int. Ed.* 2006, 45, 3760. Not only are synthetic routes to Z-alkenes relatively limited but such traditional approaches to unsaturated conjugated Z-polyenes as Wittig and Homer-Wadsworth-Emmons reactions, cannot be used to directly deliver unsaturated aldehydes. See (a) Smith, A. B III, Beauchamp, T. J.; LaMarche, M. J.; Kaufman, M. D.; Qiu, Y.; Arimoto, H.; Jones, D. R.; Kobayashi, K. *J. Am. Chem. Soc.* 2000, 122, 8654. (b) Dong, D-J.; Li, H-H.; Tian, S-K. *J. Am. Chem. Soc.* 2010, 132, 5018. (c) Still, W. C.; Gennari, C. *Tetrahedron Lett.* 1983, 24, 4405. (d) Molander, G. A.; Dehmel, F. *J. Am. Chem. Soc.* 2004, 126, 10313. (e) Huang, Z.; Negishi, E-I. *J. Am. Chem. Soc.* 2007, 129, 14788. (f) Belardi, J. K.; Micalizio, G. C. *J. Am. Chem. Soc.* 2008, 130, 16870. (g) Lindlar, H.; Dubuis, R. *Org Synth.* 1966, 46, 89. (h) Randl, S.; Gessler, S.; Wakamatsu, H.; Blechert, S. *Synlett* 2001, 430. (i) Kang, B.; Kim, D-H.; Do, Y.; Chang, S. *Org. Lett.* 2003, 5, 3041. (j) Hansen, E. C.; Lee, D. *Org. Lett.* 2004, 6, 2035. (k) Kang, B.; Lee, J, M.; Kwak, J.; Lee, Y. S.; Chang, S. *J. Org. Chem.* 2004, 69, 7661. (l) Sashuk, V.; Samojlowicz, C.; Szadkowska, A.; Grela, K. *Chem Commun.* 2008, 2468. (m) Crowe, W. E.; Goldberg, D. R. *J. Am. Chem. Soc.* 1995, 117, 5162.

The traditional metal-free approaches to unsaturated conjugated Z-polyenes, which are relatively few such as Wittig and Hornder-Wadsworth-Emmons reactions, cannot be used to directly deliver unsaturated aldehydes. The metal-catalyzed cross-coupling of two $sp^2$-hybridized reactants requires activating functionalities (e.g., organoboranes or organo-stannanes) which may be toxic, expensive and/or deleterious for the overall atom efficiency. Methods for the direct incorporation of the unsaturated α,β-carbonyl compounds with the Z-stereochemistry are limited. See (a)

Maynard, D. F.; Okamura, W. H. *J. Org. Chem.* 1995, 60, 1763. (b) Duhamel, L.; Guillemont, J.; Poirier, J-M. *Tetrahedron Lett.* 1991, 32, 4495. (c) Cahard, D.; Duhamel, L.; Lecomte, S.; Poirier, J-M. *Synlett* 1998, 12, 1399. (d) Amos, R. A.; Katzenellenbogen, J. A. *J. Org. Chem.* 1978, 43, 555.

The metal-catalyzed Claisen rearrangement offers new mechanistic paths to this classic reaction and significantly expands its synthetic utility. See (a) Tejedor, D.; Méndez-Abt, G.; Cotos, L.; García-Tellado, F. *Chem. Soc. Rev.,* 2013, 42, 458. Aluminium: (b)Bates, D. K.; Janes, M. W. *J. Org. Chem.* 1978, 43, 3856. (c) Majumdar, K. C.; Chattopadhyay, B. *Synth. Commun.* 2006, 36, 3125. (d) Majumdar, K. C.; Islam, R. *J. Heterocycl. Chem.* 2007, 44, 871. (e)Majumdar, K. C.; Islam, R. *Can. J. Chem.* 2006, 84, 1632. (f) Majumdar, K. C.; Bhattacharyya, T. *Tetrahedron Lett.* 2001, 42, 4231. (g) Majumdar, K. C.; Ghosh, M.; Jana, M.; Saha, D. *Tetrahedron Lett.* 2002, 43, 2111. (h) Majumdar, K. C.; Bandyopadhyay, A.; Biswas, A. *Tetrahedron* 2003, 59, 5289. Cu(II), Sn(IV), Ti(IV) and La(III): (i)Takanami, T.; Hayashi, M.; Suda, K. *Tetrahedron Lett.* 2005, 46, 2893. (j) Trost, B. M.; Schroeder, G. M. *J. Am. Chem. Soc.* 2000, 122, 3785. (k) Nakamura, S.; Ishihara, K.; Yamamoto, H. *J. Am. Chem. Soc.* 2000, 122, 8131. (l) Nasveschuk, C. G.; Rovis, T. *Org. Lett.* 2005, 7, 2173. (m) Nasveschuk, C. G.; Rovis, T. *Angew. Chem., Int. Ed.* 2005, 44, 3264. (n) Kaden, S.; Hiersemann, M. *Synlett* 2002, 1999. (o) Helmboldt, H.; Hiersemann, M. *Tetrahedron* 2003, 59, 4031. (p) Abraham, L.; Korner, M.; Hiersemann, M. *Tetrahedron Lett.* 2004, 45, 3647. (q) Sharghi, H.; Aghapour, G. *J. Org. Chem.* 2000, 65, 2813. (r) Bancel, S.; Cresson, P. C. *R. Acad. Sci. Ser. C.* 1970, 270, 2161. (s) Nonoshita, K.; Banno, H.; Maruoka, K.; Yamamoto, H. *J. Am. Chem. Soc.* 1990, 112, 316. (t) Sugiura, M.; Nakai, T. *Chem. Lett.* 1995, 697. (u)Akiyama, K.; Mikami, K. *Tetrahedron Lett.* 2004, 45, 7217. (v) Itami, K.; Yamazaki, D.; Yoshida, *J. Org. Lett.* 2003, 5, 2161. (w) Jamieson, A. G.; Sutherland, A. *Org. Biomol. Chem.* 2006, 4, 2932. (x)Swift, M. D.; Sutherland, A. *Org. Biomol. Chem.* 2006, 4, 3889. (y) Nakamura, I.; Bajracharya, G. B.; Yamamoto, Y. *Chem. Lett.* 2005, 34,174. (z) Sattelkau, T.; Eilbracht, P. *Tetrahedron Lett.* 1998, 39, 1905. (aa) Eilbracht, P.; Gersmeier, A.; Lennard, D.; Huber, T. *Synthesis* 1995, 330; (ab) Sattelkau, T.; Hollmann, C.; Eilbracht, P. *Synlett* 1996, 1221.(ac) Sattelkau, T.; Eilbracht, P. *Tetrahedron Lett.* 1998, 39, 9647.

When metals coordinate with π-bases, such as alkenes or alkynes, the first step of the rearrangement can be described as a 6-endo-dig cyclization that leads to a cyclic six-membered intermediate (See FIG. 1). Thus, this mode of rearrangement was termed "cyclization-mediated pathway". See (a) Henry, P. M. *Acc. Chem. Res.* 1973, 16. (b) Henry, P. M. *Adv. Organomet. Chem.* 1975, 13, 363. (c) Overman, L. E. *Angew. Chem. Int. Ed. Engl.* 1984, 23, 579. On the other hand, Lewis acids, such as $Cu^{+2}$, $Al^{+3}$ and H+ initiate the so-called "cation-accelerated oxonia Claisen" rearrangement by coordinating with oxygen (See FIG. 1). See (a) Maruoka, K.; Saito, S.; Yamamoto, H. *J. Am. Chem. Soc.* 1995, 117, 1165. (b) Stevenson, J. W. S.; Bryson. *Tetrahedron Lett.* 1982, 23, 3143. (c) Takai, K.; Mori, I.; Oshima, K.; Nozaki, H. *Bull. Chem. Soc. Jpn.* 1984, 57, 446. (d) Takai, K.; Mori, I.; Oshima, K.; Nozaki, H. *Tetrahedron* 1984, 40, 4013. (e) Takai, K.; Mori, I.; Oshima, K.; Nozaki, H. *Tetrahedron Lett.* 1981,22, 3985.

Recently, we reported a mechanistic study of Au(I)-catalyzed propargyl Claisen and allenyl vinyl ether rearrangement, where Au(I), commonly considered as an alkynophilic Lewis acid, coordinates with the oxygen and directs the Claisen rearrangement through an oxonia path. See (a) Vidhani, D. V.; Cran, J. W.; Krafft, M. E.; Manoharan, M.; Alabugin, I. V. *J. Org. Chem.* 2013, 78, 2059. (b) Vidhani, D. V.; Cran, J. W.; Krafft, M. E.; Alabugin, I. V. *Org. Biomol. Chem.,* 2013, 11, 1624. The barrier for the alternative cyclization-mediated pathway is 1.5 kcal/mol higher. Two important features of the calculated Au-catalyzed cyclization-mediated pathway includes: 1) lack of substituent effects and 2) selective stabilization of the TS for the Grob fragmentation of the six-membered intermediate by Au(I)-catalysts.

The latter effect lowers the barrier to the extent that this intermediate corresponds to a shallow inflection on the potential energy surface, so the overall process blends the characteristics of a stepwise and a concerted process. The nature of this unusual potential energy surface depends strongly on substrate-catalyst coordination and solvent, as illustrated by the successful trapping of the six-membered intermediate by nucleophilic attack of water in dioxane reported by the Toste group. See (a) Sherry, B. D.; Maus, L.; Laforteza, B. N.; Toste, D. *J. Am. Chem. Soc.* 2006, 128, 8132.

SUMMARY OF THE INVENTION

The present invention is directed to the transformation of propargyl vinyl ethers into (E,Z)-dienal compounds using a Rh(I)-catalyzed propargyl Claisen rearrangement and prototropic isomerization sequence.

In one preferred embodiment, shown below, the method of the present invention provides α,β-unsaturated aldehydes from starting reactants comprising a functionalized aldehyde and a functionalized alkyne in three steps with excellent stereoselectivity:

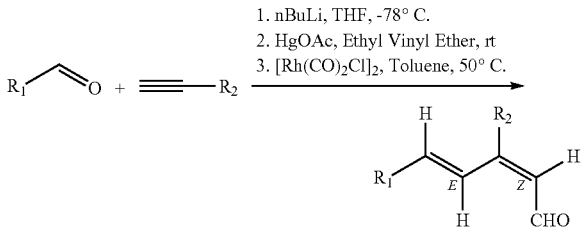

In some specific embodiments, the present invention is directed to a reaction sequence in which the reactants, products of each step, and reaction conditions of each step are as shown below. Starting reactants may include the following functionalized aldehyde and functionalized acetylide:

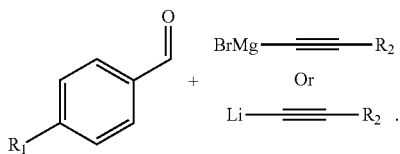

In some embodiments, the functionalized acetylide may be formed from reaction of a strong base with a functionalized alkyne. Suitable conditions for the reaction between the functionalized aldehyde and the functionalized acetylide include THF as the solvent at 0° C. or −78° C. for between 1 and 2 hrs.

In some embodiments, the product of the first step and the reactant for the second step is a functionalized propargyl, which may have the following structure:

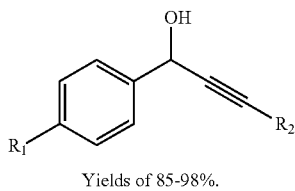

Yields of 85-98%.

In some embodiments, the product of the second step and the reactant for the third step is a functionalized propargyl vinyl ether, which may have the following structure:

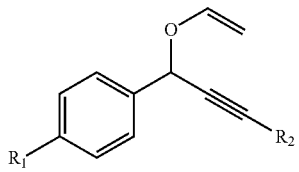

In some embodiments, suitable conditions for this reaction include 0.6% $Hg(OAc)_2$ catalyst in a concentration of 0.2M in a solvent of Ethyl vinyl ether for between 12 and 16 hrs reflux.

In some embodiments, the functionalized propargyl vinyl ether reactant from above may undergo Rh(I) catalyzed Tandem rearrangement from a functionalized allene-aldehyde compound to a functionalized (E,Z)-dienal compound, having the structures as shown below:

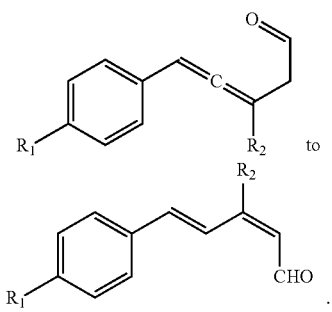

The above is one non-limiting exemplary embodiment of the method of the present invention.

Accordingly, among the provisions of the present invention may be noted is a method to synthesize an (E,Z)-dienal compound having structure (V). The method comprises contacting a compound having structure (III) with a catalyst comprising Rh(I) to thereby prepare the compound having structure (V); wherein the compounds having structures (III) and (V) have the following structures:

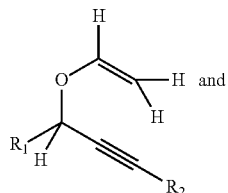 (III)

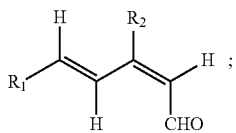 (V)

In the above structures, $R_1$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino; and $R_2$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino.

The present invention is further directed to a method to synthesize an (E,Z)-dienal compound having structure (V). The method comprises contacting a compound having structure (IV) with a catalyst comprising Rh(I) to thereby prepare the compound having structure (V);

(IV)

(V)

In the above structures, $R_1$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino; and $R_2$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino.

The present invention is still further directed to a method of preparing a compound having structure (III). The method comprises contacting a compound having structure (I) and a compound having structure (II) in the presence of a strong base; wherein the compounds having structures (I), (II), and (III) have the following structures:

(I)

(II)

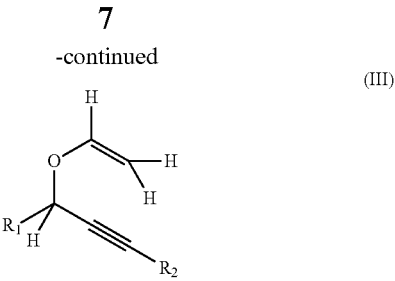
(III)

In the above structures, $R_1$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino; and $R_2$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino.

The present invention is still further directed to a method to synthesize an allene-aldehyde compound having structure (IV). The method comprises contacting a compound having structure (III) with a catalyst comprising Rh(I) to thereby prepare the compound having structure (IV); wherein the compounds having structures (III) and (IV) have the following structures:

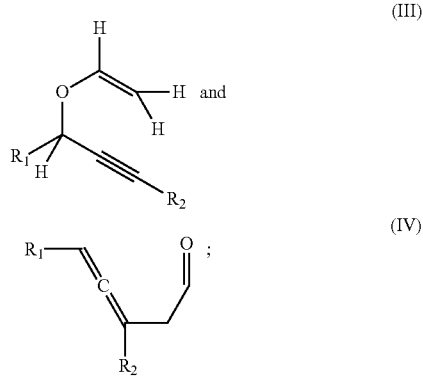

In the above structures, $R_1$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino; and $R_2$ is selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, and $C_{1-12}$ alkylamino.

Other objects and features will be in part apparent and in part pointed out hereinafter.

DETAILED DESCRIPTION OF THE EMBODIMENT(S) OF THE INVENTION

Figure 1:
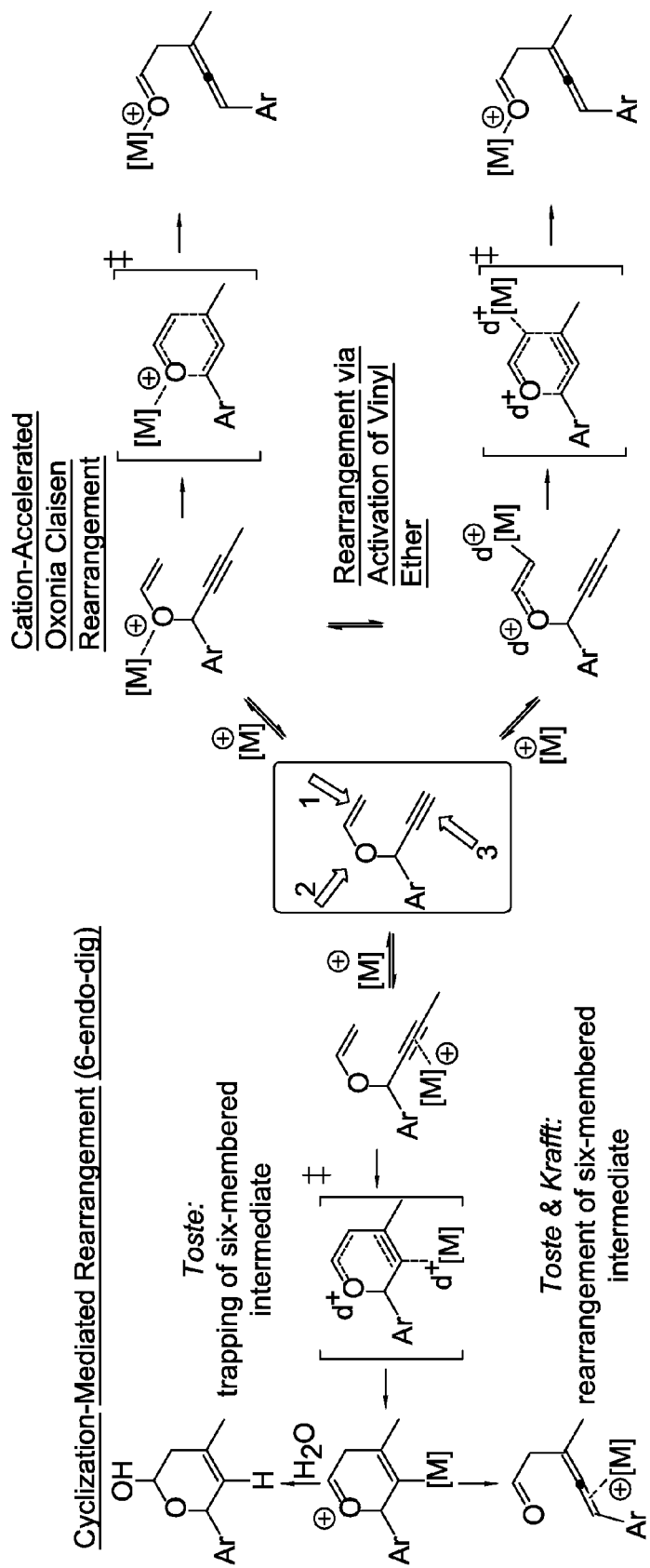
FIG. 1 depicts three mechanistic alternatives for the metal-catalyzed propargyl Claisen rearrangement. Cyclization-mediated pathway depicted on left shows two possibilities emerging from the six-membered cyclic intermediate.

The present invention is directed to an efficient process to install synthetically challenging (E,Z) conjugated double bond in three steps starting from a precursor aldehyde and a precursor alkyne with a very high stereoselectivity. The first two steps are high yielding reaction leading to the formation of a propargyl vinyl ether. The last step is a tandem process which can be interrupted to give an allene-aldehyde compound or allowed to continue to give a (E,Z)-dienal compound. This method is general for aromatic and tertiary aldehydes.

In some embodiments, the method of the present invention may be represented by the following reaction sequence:

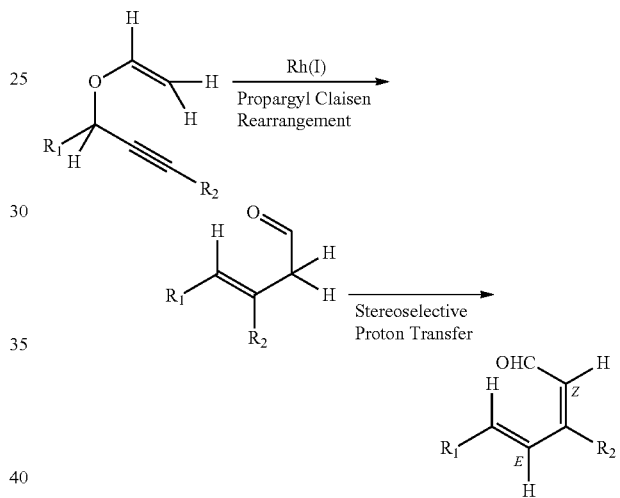

The present invention is directed to a novel Rh(I)-catalyzed approach to functionalized (E, Z) dienal compounds via tandem transformation where a stereoselective hydrogen transfer follows a propargyl Claisen rearrangement. Z-Stereochemistry of the first double bond suggests the involvement of a six-membered cyclic intermediate whereas the E-stereochemistry of the second double bond stems from the subsequent protodemetallation step giving an (E,Z)-dienal.

The combination of experiments and computations reveals unusual features of stereoselective Rh(I)-catalyzed transformation of propargyl vinyl ethers into (E, Z)-dienals. The first step, the conversion of propargyl vinyl ethers into allene aldehydes, proceeds under homogeneous conditions via the "cyclization-mediated" mechanism initiated by Rh(I) coordination at the alkyne. This path agrees well with the small experimental effects of substituents on the carbinol carbon. The key feature revealed by the computational study is the stereoelectronic effect of the ligand arrangement at the catalytic center. The rearrangement barriers significantly decrease due to the greater transfer of electron density from the catalytic metal center to the CO ligand oriented trans to the alkyne. This effect increases electrophilicity of the metal and lowers the calculated barriers by 9.0 kcal/mol. Subsequent evolution of the catalyst leads to the in-situ formation of Rh(I)-nanoclusters which catalyze stereoselective tautomerization. The intermediacy of heterogeneous catalysis by nanoclusters was confirmed by mercury poisoning, temperature-dependent sigmoidal kinetic curves, and dynamic light scattering. The combination of experiments and computations suggest that the initially formed allene-aldehyde product assists in the transformation of a homogeneous catalyst (or "a cocktail of catalysts") into nanoclusters, which, in turn, catalyze and control the stereochemistry of subsequent transformations.

In some embodiments, the method of the present invention comprises the synthesis of the propargyl vinyl ether having structure (III), as depicted below:

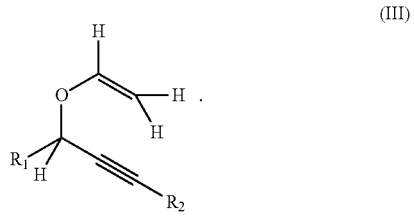

(III)

In structure (III), $R_1$ may be selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, or $C_{1-12}$ alkylamino. The alkyl, aryl, cycloalkenyl, heteroaryl, amino, and alkylamino groups may be unsubstituted. The alkylamino may be primary, secondary, or tertiary. In some embodiments, the alkyl, aryl, cycloalkenyl, heteroaryl, amino, and alkylamino groups may be substituted. Suitable substituents include $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, halogen (i.e., fluoro, chloro, bromo, iodo), hydroxy, cyano, $C_{1-12}$ alkoxy, nitro, sulfinyl, sulfonyl, amino, or $C_{1-12}$ alkylamino. The alkylamino substituent may be primary, secondary, or tertiary.

In some preferred embodiments, $R_1$ comprises a $C_{6-24}$ aryl or $C_{3-18}$ heteroaryl, which may be unsubstituted or may be further substituted with any of the above described moieties. Suitable substituents include $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, halogen (i.e., fluoro, chloro, bromo, iodo), hydroxy, cyano, $C_{1-12}$ alkoxy, nitro, sulfinyl, sulfonyl, amino, or $C_{1-12}$ alkylamino.

In structure (III), $R_2$ may be selected from the group consisting of $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, amino, or $C_{1-12}$ alkylamino. The alkyl, aryl, cycloalkenyl, heteroaryl, amino, and alkylamino groups may be unsubstituted. The alkylamino may be primary, secondary, or tertiary. In some embodiments, the alkyl, aryl, cycloalkenyl, heteroaryl, amino, and alkylamino groups may be substituted. Suitable substituents include $C_{1-12}$ alkyl, $C_{2-12}$ alkenyl, $C_{2-12}$ alkynyl, $C_{1-12}$ cycloalkyl, $C_{1-12}$ cycloalkenyl, $C_{6-24}$ aryl, $C_{3-18}$ heteroaryl, halogen (i.e., fluoro, chloro, bromo, iodo), hydroxy, cyano, $C_{1-12}$ alkoxy, nitro, sulfinyl, sulfonyl, amino, or $C_{1-12}$ alkylamino. The alkylamino substituent may be primary, secondary, or tertiary.

In some preferred embodiments, $R_2$ comprises a $C_{6-24}$ aryl or $C_{3-18}$ heteroaryl, which may be unsubstituted or may be further substituted with any of the above described moieties. Suitable substituents include $C_{1-12}$ alkyl, $C_{2-12}$ alkenyl, $C_{2-12}$ alkynyl, $C_{3-12}$ cycloalkyl, $C_{3-12}$ cycloalkenyl, $C_{6-24}$ aryl, $C_{3-18}$ heteroaryl, halogen (i.e., fluoro, chloro, bromo, iodo), hydroxy, cyano, $C_{1-12}$ alkoxy, nitro, sulfinyl, sulfonyl, amino, or $C_{1-12}$ alkylamino.

In some embodiments, $R_1$ and $R_2$ may be the same. In some embodiments, $R_1$ and $R_2$ may be different.

In the context of the present specification, unless otherwise stated, an alkyl substituent group or an alkyl moiety in a substituent group may be linear or branched. Examples of $C_{1-12}$ alkyl groups/moieties include methyl, ethyl, n-propyl, isopropyl, n-butyl, iso-butyl, tert-butyl, n-pentyl, iso-pentyl, neopentyl, n-hexyl, isohexyl, neohexyl, n-heptyl, isoheptyl, neoheptyl, n-octyl, isooctyl, neooctyl, n-nonyl, n-decyl, n-undecyl, n-dodecyl, etc. The substituent group may comprise a double bond, e.g., $C_{2-12}$ alkenyl, a triple bond, e.g., $C_{2-12}$ alkynyl, or may comprise more than one double bond.

In the context of the present specification, unless otherwise stated, an alkoxy substituent group or an alkoxy moiety in a substituent group may be linear or branched. Examples of $C_{1-12}$ alkoxy groups/moieties include methoxy, ethoxy, n-propoxy, isopropoxy, n-butoxy, iso-butoxy, tert-butoxy, n-pentoxy, iso-pentoxy, neopentoxy, n-hexoxy, etc.

In the context of the present specification, unless otherwise stated, a hydroxyalkyl substituent group or a hydroxyalkyl moiety in a substituent group may be linear or branched. Examples of $C_{1-6}$ hydroxyalkyl groups/moieties include methyl, ethyl, n-propyl, isopropyl, n-butyl, iso-butyl, tert-butyl, n-pentyl, n-hexyl, etc, each of which comprises at least one hydroxyl group substituent in place of a hydrogen.

Halogen or halo encompasses fluoro, chloro, bromo, and iodo substituents.

In the context of the present specification, cycloalkyl is a non-aromatic ring that can comprise one, two or three non-aromatic rings, and is, optionally, fused to a benzene ring (for example to form an indanyl, or 1,2,3,4-tetrahydronaphthyl ring). Cycloalkyl may comprise from 3 to 12 carbon atoms. Examples of cycloalkyl include cycobutyl, cyclopentyl, cyclohexyl, cycloheptyl, cyclooctyl, bicyclo[2.2.1]heptyl, cyclopentenyl, cyclohexenyl, or adamantyl, among others.

In the context of the present specification, cycloalkenyl is a non-aromatic ring that can comprise one, two or three non-aromatic rings, and is, optionally, fused to a benzene ring (for example to form an indanyl, or 1,2,3,4-tetrahydronaphthyl ring). Cycloalkenyl may comprise from 3 to 12 carbon atoms. Examples of cycloalkenyl include cyclopropenyl, cycobutenyl, cyclopentenyl, cyclohexenyl, cycloheptenyl, cyclooctenyl, etc.

In the context of the present invention, aryl encompasses aromatic rings, which may be fused or unfused to other aromatic or cycloalkyl rings. Aryl may comprise from 6 to 24 carbon atoms. Examples or aryl include benzene, naphthalene, acenaphthene, anthracene, benz[a]anthracene, benzo[a]pyrene, benzo[e]pyrene, chrysene, indeno(1,2,3-cd)pyrene, phenanthrene, pyrene, coronene, fluorene, and the like.

In the context of the present specification, heterocyclic ring is an aromatic or non-aromatic ring having from three to eight total atoms forming the ring system. The atoms within the ring system comprise carbon and at least one of nitrogen, sulfur, and oxygen. A heterocyclic ring may be fused to a homocyclic ring or another heterocyclic ring. The fused ring system may be aromatic or non-aromatic. Heteroaryl may comprise from 3 to 24 carbon atoms. Examples include aziridine, azirine, oxirane, oxirene, thirane, thiirene, azetidine, azete, oxetane, oxete, thietane, thiete, diazetidine, dioxetane, dioxete, dithietane, dithiete, pyrrolidine, pyrrole, tetrahydrofuran, furan, thiolane, thiophene, imidazolidine, imidazole, pyrazolidine, pyrazole, oxasolidine, oxazole, isoxazolidine, isoxazole, piperidine, pyridine, oxane, pyran, thiane, thiopyran, piperazine, diazines, morpholine, oxazine, etc.

In some embodiments, the compound having structure (III) may synthesized by contacting a compound having structure (I) and a compound having structure (II) according to the following sequence:

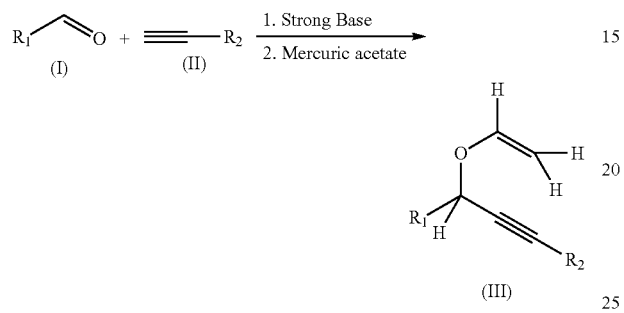

wherein $R_1$ and $R_2$ are as defined above with respect to Structure (III).

The reaction occurs in the presence of a strong base. Suitable strong bases for use in the method of the present invention include organolithium compounds, including alkyl lithium compounds, such as n-butyl lithium, sec-butyl lithium, isopropyl lithium, etc., or a Grignard reagent, such as an organomagnesium halide. The n-butyl lithium may be provided in an alkane (e.g., pentane, hexane, heptane) solution or in an ether (e.g., diethyl ether, tetrahydrofuran) solution.

In some embodiments, the structure (III) may synthesized by contacting a compound having structure (I) and a compound having structure (II) according to the following sequence:

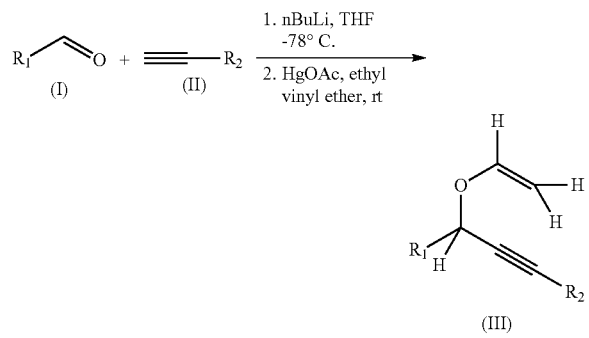

wherein $R_1$ and $R_2$ are as defined above with respect to Structure (III).

According to some embodiments of the method of the present invention, a compound having structure (III) is contacted with a catalyst comprising Rh(I) to thereby prepare an (E,Z)-dienal compound having structure (V):

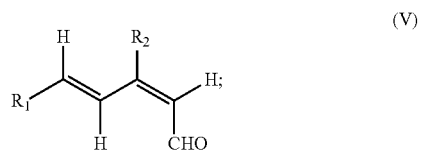

wherein $R_1$ and $R_2$ are as defined above with respect to Structure (III).

According to some embodiments of the method of the present invention, the compound having structure (III) is contacted with a catalyst comprising Rh(I) in order to prepare a compound having structure (IV):

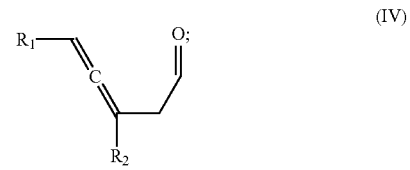

wherein $R_1$ and $R_2$ are as defined above with respect to Structure (III). In some embodiments of the method of the present invention, the compound having structure (IV), i.e., a compound comprising allene-aldehyde, may be isolated. In some embodiments of the method of the present invention, the compound having structure (IV), i.e., a compound comprising allene-aldehyde may undergo further rearrangement into the compound having structure (V).

According to some embodiments of the method of the present invention, a compound having structure (IV) is contacted with a catalyst comprising Rh(I) to thereby prepare an (E,Z)-dienal compound having structure (V):

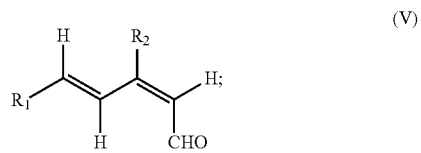

wherein $R_1$ and $R_2$ are as defined above with respect to Structure (III).

Applicable Rhodium(I) catalysts include Acetylacetonatobis(ethylene)rhodium(I) 95%, (Acetylacetonato)(1,5-cyclooctadiene)rhodium(I) 99%, (Acetylacetonato)(1,5-cyclooctadiene)rhodium(I) 99%, (Acetylacetonato)(1,5-cyclooctadiene)rhodium(I) 99%, (Acetylacetonato)dicarbonylrhodium(I) 98%, (Acetylacetonato)dicarbonylrhodium(I) 98%, (Acetylacetonato)(norbornadiene)rhodium(I), (Bicyclo[2.2.1]hepta-2,5-diene)[1,4-bis(diphenylphosphino)butane]rhodium(I) tetrafluoroborate, Bicyclo[2.2.1]hepta-2,5-diene-rhodium(I) chloride dimer 96%, Bicyclo[2.2.1]hepta-2,5-diene-rhodium(I) chloride dimer, Bis(acetonitrile)(1,5-cyclooctadiene)rhodium(I)tetrafluoroborate, [(Bisacetonitrile)(norbornadiene)]rhodium(I) hexafluoroantimonate 97%, Bis(1,5-cyclooctadiene)rhodium(I) tetrafluoroborate hydrate 97%, Bis(1,5-cyclooctadiene)rhodium(I) tetrafluoroborate hydrate, Bis(1,5-cyclooctadiene)rhodium(I) hexafluoroantimonate 97%, Bis(1,5-cyclooctadiene)rhodium(I) tetrafluoroborate, Bis(1,5-cyclooctadiene)rhodium(I) tetrakis[bis(3,5-trifluoromethyl)phenyl]borate, Bis(1,5-cyclooctadiene)

rhodium(I) trifluoromethanesulfonate 98%, Bis(1,5-cyclooctadiene)rhodium(I) trifluoromethanesulfonate, 1,1'-Bis(diisopropylphosphino)ferrocene(cod)Rh-phosphotungstic acid on silica gel 100-200 mesh, extent of labeling: 0.020 mmol/g Rh loading, Bis[(10,11-η)-5-[(11bS)-dinaphtho[2,1-d:1',2'-f][1,3,2]dioxaphosphepin-4-yl-κP⁴]-5H-dibenz[b,f]azepine]rhodium(I) tetrafluoroborate salt 97%, [1,4-Bis(diphenylphosphino)butane](1,5-cyclooctadiene)rhodium(I) tetrafluoroborate 98%, Bis(norbornadiene)rhodium(I) tetrafluoroborate, Bis(norbornadiene)rhodium(I) trifluoromethanesulfonate 97%, Bis[rhodium(a,a,a', a'-tetramethyl-1,3-benzenedipropionic acid)] 96%, Bis(triphenylphosphine)rhodium(I) carbonyl chloride 99.9%, Chlorobis(cyclooctene)rhodium(I),dimer 98%, Chloro[bis[(10,11-η)-5H-dibenzo[a,d]cyclohepten-5-yl]amine-κN] rhodium(I) dimer, Chloro(1,5-cyclooctadiene)rhodium(I) dimer 98%, Chloro(1,5-hexadiene)rhodium(I),dimer 98%, Chlorotris[3,3',3"-phosphinidynetris(benzenesulfonato)] rhodium(I) nonasodium salt hydrate 99%, (1,5-Cyclooctadiene)bis(triphenylphosphine)rhodium(I) hexafluorophosphate dichloromethane complex (1:1), (1,5-Cyclooctadiene) (8-quinolinolato)rhodium(I) 97%, Dicarbonyl (pentamethylcyclopentadienyl)rhodium(I) 99%, Di-μ-chloro-tetracarbonyldirhodium(I) 97%, Di-μ-chlorotetraethylene dirhodium(I), Dirhodium tetracaprolactamate 97%, Hexarhodium(0) hexadecacarbonyl Rh 57-60% (approx.), Hydridotetrakis(triphenylphosphine)rhodium(I), Hydroxy(cyclooctadiene)rhodium(I) dimer 95%, Methoxy(cyclooctadiene)rhodium(I) dimer, Triphenylphosphine(2,5-norbornadiene)rhodium(I) tetrafluoroborate, polymer-bound Fibre-cat®, [Tris(dimethylphenyl-phosphine)](2,5-norbornadiene)rhodium(I) hexafluorophosphate 97%, Tris(triphenylphosphine)rhodium(I) carbonyl hydride 97%, Tris(triphenylphosphine) rhodium(I) chloride 99.9% trace metals basis, Tris(triphenylphosphine)rhodium(I) chloride, and Tris(triphenylphosphine)rhodium(I) chloride polymer-bound ~1% Rh.

Suitable Rh(I) catalysts include di-μ-chloro-tetracarbonyldirhodium(I) [Rh(CO)₂Cl]₂, Bis(triphenylphosphine) rhodium(I) carbonyl chloride, tris(triphenylphosphine)rhodium (I) carbonyl hydride, tris(triphenylphosphine)rhodium (I) carbonyl chloride, among other Rh(I) catalysts.

The most unusual feature of this invention is the generation of in-situ Rh(I)-nanoclusters which catalyzes the stereoselective isomerization of allene-aldehyde. The onset of isomerization does not occur until the complete conversion of substrate, propargyl vinyl ether, into the allene-aldehyde intermediate. This is the first example of a shift from homogeneous to heterogeneous catalysis in one pot. Thus, the rearrangement can either be stopped at the homogeneous step to isolate allene-aldehyde or allowed to continue under heterogeneous conditions to give (E, Z) dienal with high stereoselectivity.

To verify the involvement of Rh(I)-nanoclusters in the prototropic rearrangement, we performed dynamic light scattering (DLS) experiments on the allene-aldehyde derived from the phenyl substituted substrate 2 (See Table 3). This technique is used to determine the size-distribution of particles in suspension. Typically, in the DLS experiment, the solution containing the nanoclusters is irradiated with the monochromatic light from the laser and the intensity of the light diffracted by the nanocluster is measured. Since the scattered light from nanoclusters undergoes constructive and destructive interference by the surrounding scatterers, a complex intensity fluctuation pattern containing a detailed information about the time scale of the movement of the scatterers emerges. To process this information, a mathematical tool called autocorrelation, is used to identify a repeating pattern burned under the complex signal.

$$g^2(q;\tau) = \frac{\langle I(t)I(t+\tau)\rangle}{\langle I(t)\rangle^2}$$

$g^2(q;\tau)$: Autocorrelation function
$q$: Wave vector
$\tau$: Delay time
$I$: Intensity Generally, data is interpreted only when the plot of intensity vs. time shows a smooth and continuous decay of intensity for autocorrelation function. Such plots are classified as "proceed-category". In the present study, the catalyst and the substrate solutions did not show the presence of nanoclusters. Interestingly, the reaction mixture at 50% conversion of allene-aldehyde into respective (E, Z)-dienal showed the presence of 170 nm nanoclusters. Moreover, low observed polydispersity (5%) suggested that the solution consisted of uniformly sized particles.

Accordingly, experimental and computational analysis of the tandem process suggests a cascade transformation that evolves from homogeneous to heterogeneous catalysis. The Rh(I)-catalyzed propargyl Claisen rearrangement involves homogeneous catalysis whereas the subsequent prototropic rearrangement shows the telltale signs of heterogeneous catalysis.

In this work, we disclose a tandem transformation of propargyl vinyl ethers into dienals, where stereochemistry at both double bonds in the product is defined simultaneously by the nature of a common cyclic intermediate located at the Claisen rearrangement hypersurface connecting propargyl vinyl ethers with allene-aldehyde. Trapping of such cyclic structure via deprotonation coupled with the Grob fragmentation should lead to the conjugated dienals with E,Z-stereochemistry: the Z-geometry at the α,β-alkene is defined by the syn arrangement of the endocyclic σ-bonds whereas the E-stereochemistry at γ,δ-alkene stems from the syn-arrangement of the exocyclic C-R1 and C-M bonds and proto-demetallation with retention of configuration. See the following general reaction sequence:

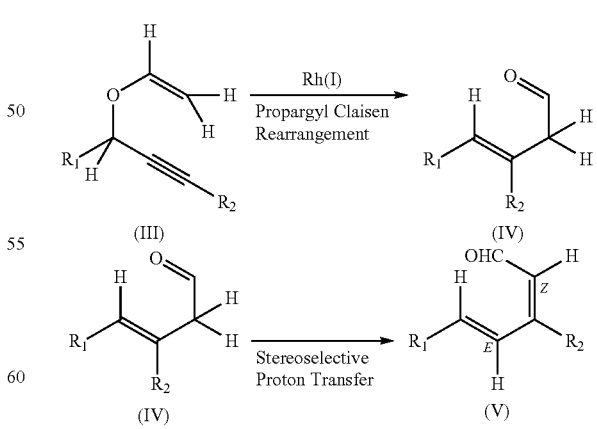

The (E, Z)-dienal only starts to form after the complete conversion of propargyl vinyl ether into the allene-aldehyde. Accordingly, intermediate (IV) can be isolated without proceeding to the metal-catalyzed propargyl Claisen rearrangement into the (E, Z)-dienal having structure (V). The mechanism of the six-membered intermediate in the metal-catalyzed propargyl Claisen rearrangement into (E, Z)-dienals defines stereochemistry in both double bonds of the product is thought to proceed as follows:

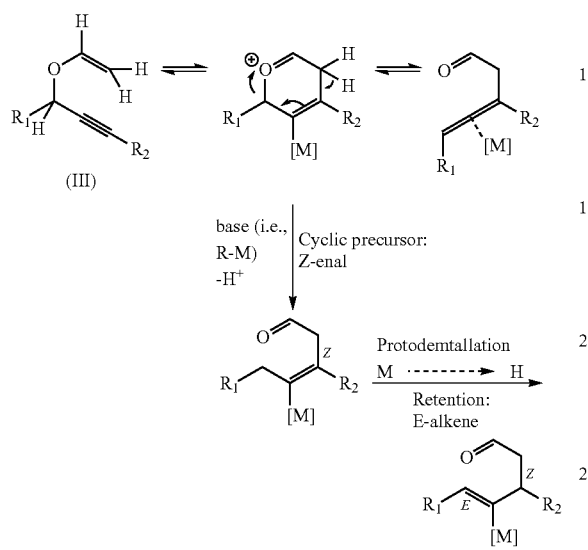

Au(I)-catalyzed Claisen rearrangements of propargyl and allenyl vinyl ethers were first reported by the groups of Toste and Krafft, respectively. See Sherry, B. D.; Toste, F. D. *J. Am. Chem. Soc.* 2004, 126, 15978. (b) Mauleon, P.; Krinsky, J. L.; Toste, F. D. *J. Am. Chem. Soc.* 2009, 131, 4513; and Krafft, M. E.; Hallal, K. M.; Vidhani, D. V.; Cran, J. W. *Org. Biomol. Chem.*, 2011, 9, 7535. In a recent mechanistic study of these two rearrangements, we found that although the cyclic intermediate does not correspond to an energy minimum at the DFT potential energy hypersurface in the presence of $R_3PAuSbF_6$-catalyst, the details of Au . . . substrate interactions at this stage suggest that slight modification in the nature of the catalyst may be sufficient for creating and trapping such cyclic structure. See (a) Vidhani, D. V.; Cran, J. W.; Krafft, M. E.; Manoharan, M.; Alabugin, I. V. *J. Org. Chem.* 2013, 78, 2059; (b) Vidhani, D. V.; Cran, J. W.; Krafft, M. E.; Alabugin, I. V *Org. Biomol. Chem.*, 2013, 11, 1624; and (c) Sherry, B. D.; Maus, L.; Laforteza, B. N.; Toste, F. D. *J. Am. Chem. Soc.* 2006, 128, 8132.

Although trapping via deprotonation has not been reported so far and our initial attempts with weak bases such as aniline led to deactivation of the Au-catalyst, we were further encouraged by the results of Toste and coworkers who found that the use of multinuclear Au-catalyst provides access to such cyclic structure trappable by reaction with external nucleophiles.

Because the equilibrium between the metal-alkyne, metal-vinyl ether and metal-oxygen complexes should strongly depend on the nature of metal, we scanned a number of transition metal catalysts. Herein, we report that stereoselective tandem isomerization of propargyl vinyl ethers to (E,Z)-dienals can be achieved using Rh(I)-catalysis.

Screening of commonly used transition metals showed that Au-based catalysts promote the Claisen rearrangement step but only AuCl is efficient in moving the cascade further (Table 1). However, the stereoselectivity of the final step was, at best, modest. Pd-based catalysts were only successful in promoting the first step. The hard Lewis acids such as $Cu(OTf)_2$, $Zn(OTf)_2$ and $Sc(OTf)_3$ were even less efficient. On the other hand, $[Rh(CO)_2Cl]_2$ displayed remarkable reactivity, effectively promoting both the allene formation and its subsequent rearrangement into the desired (E,Z)-dienal 2a (Table 1, entry 14). Donor phosphine ligands at the Rh center eliminated the catalytic activity (entry 15).

TABLE 1

Catalyst screening

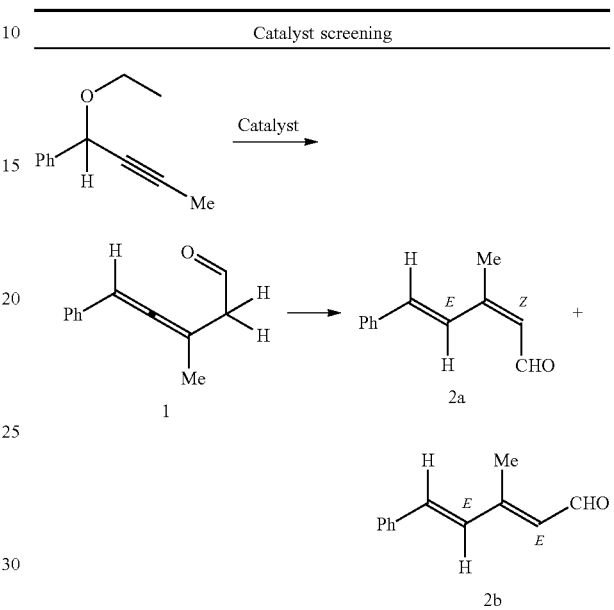

| entry | catalyst | 1 | 2a | 2b |
|---|---|---|---|---|
| 1 | AuCl | —[b] | 28 | 72 |
| 2 | $AuCl_3$ | 72 | 9 | 17 |
| 3 | $Ph_3PAuSbF_6$ | 93 | 4 | 3 |
| 4 | $[Au]SbF_6$ | 100 | — | — |
| 5 | $IPr-AuSbF_6$ | 100 | — | — |
| 6 | $PdCl_2$ | 12 | — | — |
| 7 | $Pd(PPh_3)_2Cl_2$ | 100 | — | — |
| 8 | $Pd(PPh_3)_4$ | 8 | 3 | — |
| 9 | $Pd(PhCN)_2Cl_2$ | 100 | — | — |
| 10 | $PtCl_2$ | — | — | — |
| 11 | $Cu(OTf)_2$ | 16 | — | — |
| 12 | $Zn(OTf)_2$ | 15 | — | — |
| 13 | $Sc(OTf)_3$ | 10[c] | — | — |
| 14 | $[Rh(CO)_2Cl]_2$ | —[b] | 98 | 2 |
| 15 | $(PPh_3)_3RhCl$ | — | — | — |

[a]Standard reaction conditions: 0.1M Substrate in toluene-d8 at 50° C. in the presence of 10% metal catalyst for 24 hours. Ratios determined by proton NMR.
[b]Complete conversion of substrate into 1 was observed, followed by its full transformation into 2a and 2b.

Remarkably, $[Rh(CO)_2Cl]_2$ and AuCl provided cascade products in high yields but with the opposite stereochemistry. Table 2 summarizes further optimization of the Rh-catalyzed reactions. Coordinating solvents such as acetonitrile form a strong complex with Rh(I) and deactivate the catalyst. See (a) Costa, M.; Della Pergola, R.; Fumagalli, A.; Laschi, F.; Losi, S.; Macchi, P.; Sironi, A.; Zanello, P. *Inorg. Chem.*, 2007, 46, 552. (b) Fumagalli, A.; Martinengo, S.; Ciani, G.; Moret, M.; Sironi A. *Inorg. Chem.* 1992, 31, 2900. Rearrangement in the mildly coordinating $CH_2Cl_2$ was sluggish (10% dienal 2a and 35% allene-aldehyde 1). The reaction in tetrahydrofuran gave 90% allene-aldehyde 1 at the room temperature and proceeded slowly towards the 3:1 mixture of the dienals at 50° C.

TABLE 2

Optimization studies

| entry | solvent | temp | 1 | 2a | 2b |
|---|---|---|---|---|---|
| 1 | $CD_3CN$ | 25 | N.R | — | — |
| 2 | $CD_3CN$ | 50 | N.R | — | — |
| 3 | $CD_3NO_2$ | 25 | Trace[c] | — | — |
| 4 | THF-$d_8$ | 25 | 90 | — | — |
| 5 | THF-$d_8$ | 50 | 89 | 8 | 3 |
| 6 | $CD_2Cl_2$ | 25 | 35 | 10 | — |
| 8 | Toluene-$d_8$ | 25 | 100 | — | — |
| 7 | Toluene-$d_8$ | 50 | —[b] | 98 | 2 |
| 8 | $C_6D_6$ | 25 | 95 | — | — |
| 9 | $C_6D_6$ | 50 | —[b] | 95 | 5 |

[a] Standard reaction conditions: All reactions were performed at 0.1M concentration in the presence of 10% [Rh(CO)$_2$Cl]$_2$. Relative ratios were determined by proton NMR.
[b] Complete conversion of enol ether into 1 was observed that was subsequently fully converted into 2a and 2b.
[c] Significant decomposition of substrate was observed.

On the other hand, conversions in benzene and toluene were clean and proceeded in high yield and remarkable E,Z-selectivity for substrates with the broad range of aromatic substituents at the carbinol carbon. Both donors and acceptors work well. Furthermore, other sp$^2$-substituents are also compatible with the cascade. For example, a cyclohexenyl substituted substrate gave dienal product in 62% yield with excellent (E,Z)-stereoselectivity. Furthermore, the cascade tolerates steric hindrance—even with the bulky substituents such as t-butyl and mesityl, the Claisen products are quickly formed at 50° C. and smoothly converted to the dienals in ~80% yield and excellent stereoselectivity upon further heating.

The following Table 3 provides examples of starting propargyl vinyl ethers with products that may be obtained therefrom. The present invention is not limited to this list of propargyl vinyl ethers and their subsequent (E,Z)-dienal compounds, but rather, the method may be suitable for preparing a broad array of (E,Z)-dienal compounds.

TABLE 3

List of substrates used for the kinetic study.

| Substrate | Product |
|---|---|
| (1a) | (1) |
| (2a) | (2) |
| (3a) | (3) |
| (4a) | (4) |
| (5a) | (5) |

In some embodiments, the following exemplary compounds provided in Table 4 may be prepared by the method of the present invention. The present invention is not limited to this list of compounds, but rather, the method may be suitable for preparing a broad array of (E,Z)-dienal compounds.

TABLE 4

Products of Rh(I)-catalyzed rearrangements obtained from their respective propargyl vinyl ethers.

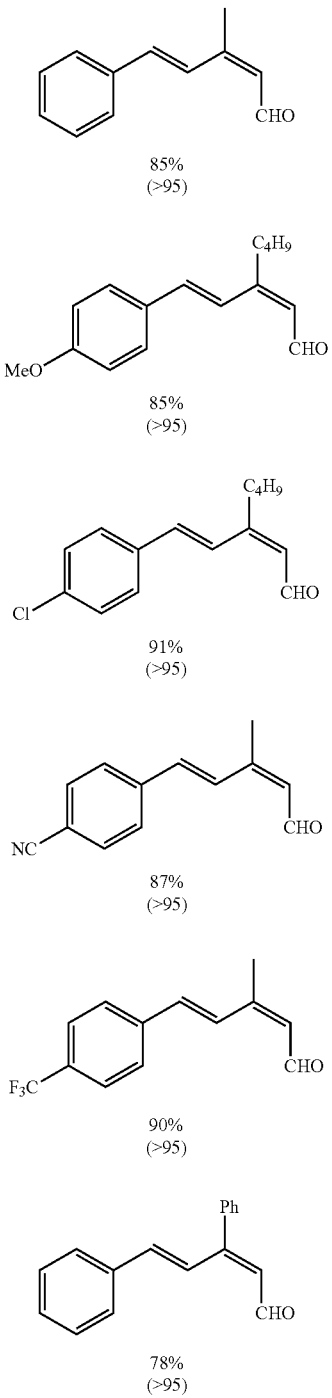

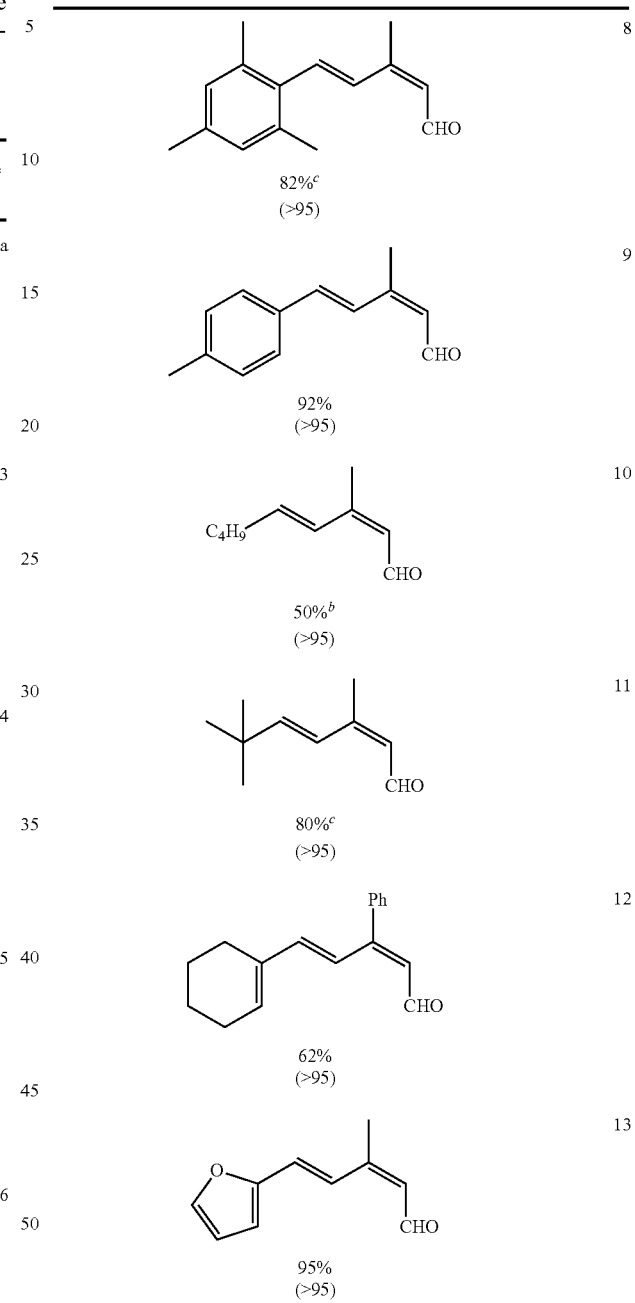

Percentages correspond to the isolated yields.
In the above list of products, values in parenthesis show percentage of E, Z isomer determined by proton NMR.
[a]Reaction Conditions: 0.1M solution of 0.1 mmol propargyl vinyl ether in toluene in the presence of 10% [Rh(CO)$_2$Cl]$_2$ at 50° C.
[b]Rearranges further into a mixture of products.
[c]Requires 70° C.

The current limitations of this process seem to be associated with the possibility of further prototropic isomerizations. For substrates with a n-butyl group at the carbinol carbon, the dienal yields decreases to ~50% due to formation of several non-identified non-polar by-products. In the presence of a secondary (cyclohexyl) substituent, formation of Claisen product proceeded efficiently (>90%) at 50° C. but its subsequent rearrangement at 70° C. produced only a small amount of (E, Z) dienal product together with unknown non-polar products. The cyclopropyl-substituted substrate was unreactive in the presence of Rh(I) at 50° C. and decomposed at higher temperatures.

DFT calculations at the M05-2X/LANL2DZ level suggest that the electron rich vinyl ether dissociates 16 electron Rh(I)-dimer to form a 16 electron Rh(I)-VE complex which is expected to be the catalyst resting state. See FIG. 2. The uncomplexed monomeric 14 electron pre-catalyst, $Rh(CO)_2$Cl is unlikely to be persistent. See Pitcock, Jr, W. H.; Lord, R. L.; Baik, M-H. *J. Am. Chem. Soc.* 2008, 130, 5821.

Figure 2:
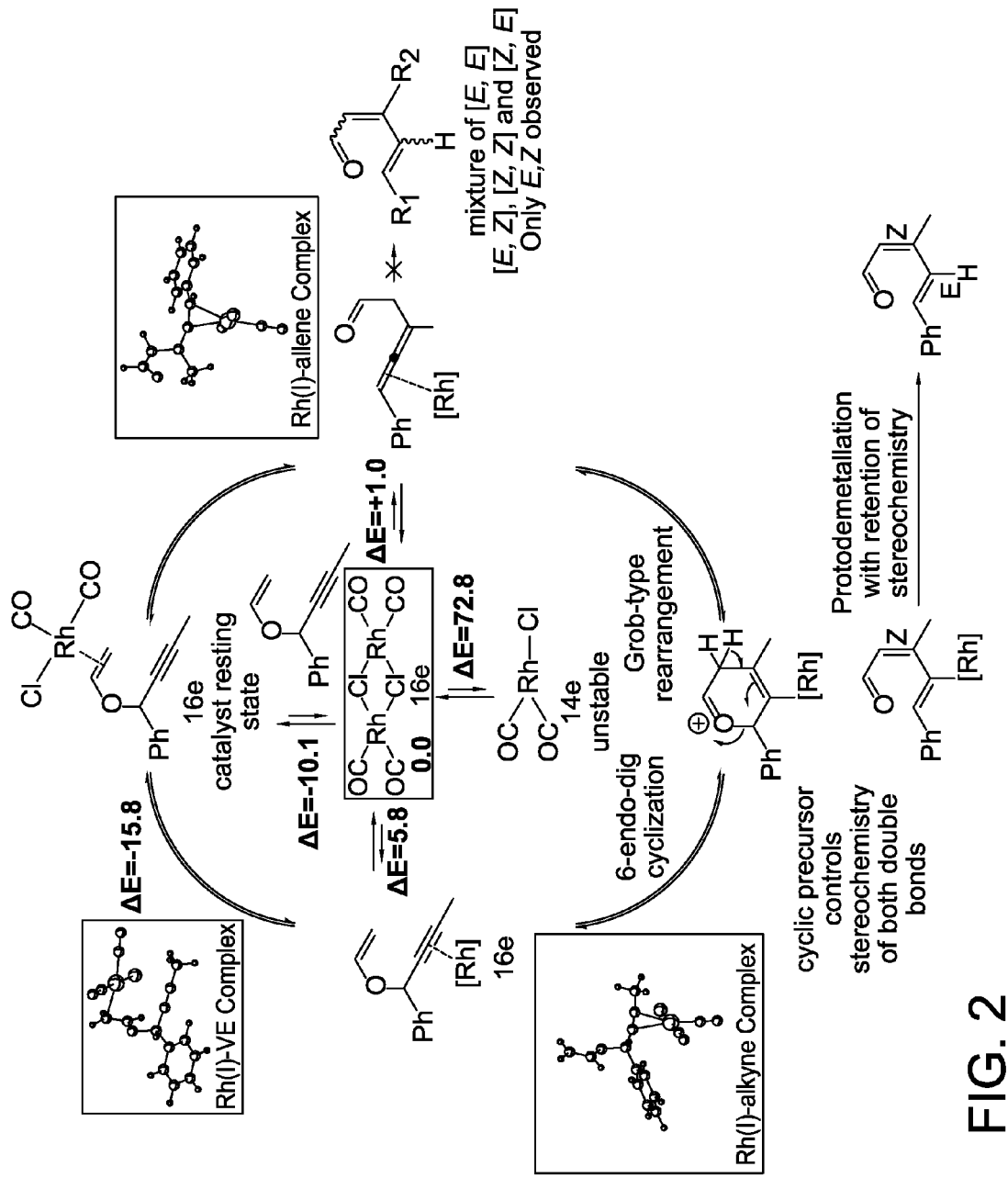
FIG. 2 depicts the proposed catalytic cycle. ΔE values correspond to the PCM-SCRF-M05-2X/LANL2DZ energies of the intermediate species relative to the uncomplexed Rh(I)-dimer.

Additional information regarding the mechanism of this isomerization was provided by DFT calculations. They revealed that the most stable complex produced via coordination of Rh(I) with the vinyl ether is catalytically unproductive due to high barrier (FIG. 2, TS1: 41.2 kcal/mol). DFT computations performed at M05-2X level suggests that the less stable complexes formed via coordination of Rh(I) with the alkyne or the oxygen rearrange via considerably lower barriers. See (a) Zhao, Y.; González-García, N.; Truhlar, D. G. *J. Phys. Chem. A* 2005, 109, 2012. (b) Zhao, Y.; Truhlar, D. G. *Org. Lett.* 2007, 9, 1967. (c) Schultz, N.; Zhao, Y.; Truhlar, D. G. *J. Phys. Chem. A* 2005, 109, 11127.

Coordination of Rh(I) to the oxygen initiates the oxonia-Claisen rearrangement which proceeds via a dissociative-TS with 23.4 kcal/mol barrier (See FIG. 2, TS2). Coordination of Rh(I) with the alkyne directs rearrangement via a very low 9.7 kcal barrier (See FIG. 3, TS3). Even after the Curtin-Hammett correction, the latter route offers the lowest energy path for the Claisen rearrangement with the barrier of 17.7 kcal/mol (See FIG. 3). For the stereoelectronic reasons for the endo-selectivity in metal-catalyzed reactions ("LUMO umpolung), see: (a) Alabugin, I. Gilmore, K.; Manoharan, M. *J. Am. Chem. Soc.* 2011, 133, 12608. Reviews: (b) Gilmore, K.; Alabugin, I.V. *Chem. Rev.* 2011, 111, 6513. (c) Peterson, P. W.; Mohamed, R. K.; Alabugin, I. V. *Eur. J. Org. Chem.,* 2013, 2013, 2505. Selected applications: (d) Zhao, J.; Hughes, C. O.; Toste, F. D. *J. Am. Chem. Soc.* 2006, 128, 7436. (e) Byers, P. M.; Rashid, J. I.; Mohamed, R. K.; Alabugin, I. V. *Org. Lett.* 2012, 14, 6032. (f) Hashmi, A. S. K.; Braun, I.; Rudolph, M.; Rominger, F. *Organometallics* 2012, 31, 644. (g) Naoe, S.; Suzuki, Y.; Hirano, K.; Inaba, Y.; Oishi, S.; Fujii, N.; Ohno, H. *J. Org. Chem.* 2012, 77, 4907. (i) Hansmann, M. M.; Rudolph, M.; Rominger, F.; Hashmi, A. S. K. *Angew. Chem., Int. Ed.* 2013, 52, 2593.

Although the interception of the pericyclic pathway is conceptually interesting and increasingly utilized in the design of cascade organic transformations, the six-membered intermediate in the "cyclization-mediated pathway" is often elusive and its presence and lifetime depend on the intricate details of transition state complexation with the catalyst. Selected precedents for the interception of pericyclic pathways: Discovery of aborted pericyclic reactions: (a) Gilmore, K.; Manoharan, M.; Wu, J.; Schleyer, P. v. R; Alabugin, I. V. *J. Amer. Chem. Soc.* 2012, 134, 10584 . Interrupted pericyclic reactions: (b) Navarro-Vazquez, A.; Prall, M.; Schreiner, P. R. *Org. Lett.* 2004, 6, 2981. Recent reviews: (c) Graulich, N.; Hopf, H.; Schreiner, P. R. *Chem. Soc. Rev.* 2010, 39, 1503. (d) Mohamed, R. K.; Peterson, P. W.; Alabugin, I. V. *Chem. Rev.,* 2013, http://dx.doi.org/10.1021/cr4000682. For the special properties of alkynes facilitating the design of such reactions, see: Alabugin, I. V.; Gold, B. *J. Org. Chem.* 2013, 78, http://pubs.acs.org/doi/abs/10.1021/jo401091w. For example, we had shown in our earlier work on Au-catalyzed rearrangement how coordination of Au stabilizes TS for the subsequent Grob-type fragmentation into the allene-aldehyde product to the extent that the intermediate corresponds to a shallow inflection at the potential energy surface. On the other hand, Siebert and Tantillo found that a combination of transition-state complexation with resonance stabilization converts a TS into a cyclic intermediate in Pd-promoted Cope rearrangement. See Siebert, M. R.; Tantillo, D. J. J. *Am. Chem. Soc.* 2007, 129, 8686.

Figure 3:
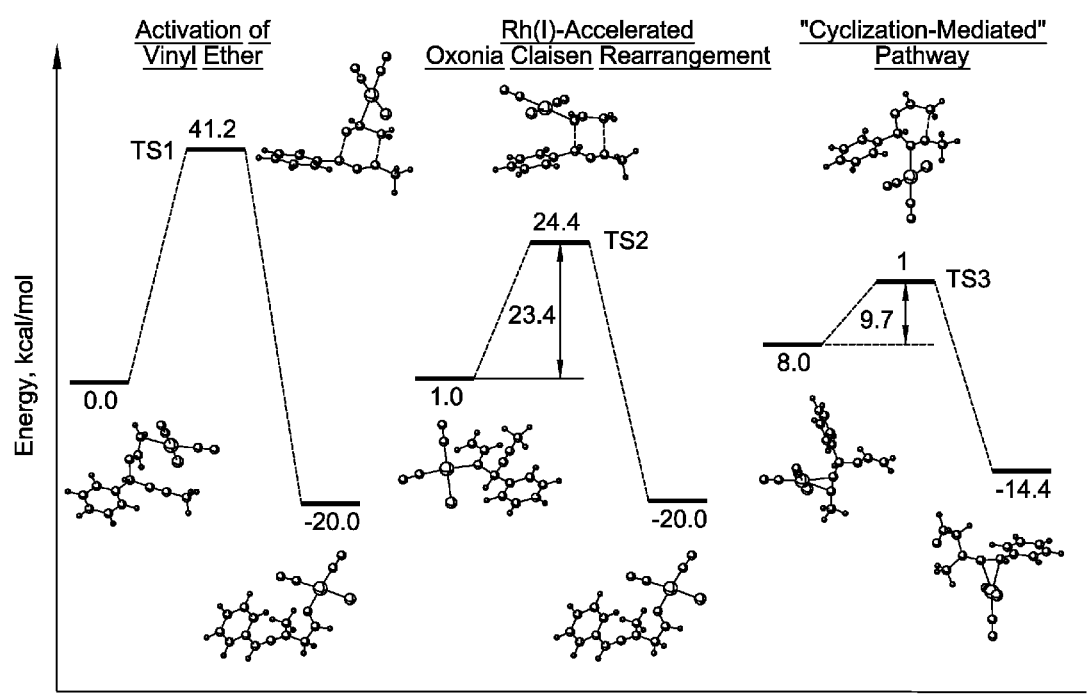
FIG. 3 illustrates Curtin-Hammett analysis of the three mechanisms. Energies in toluene were calculated at the PCM-SCRF-M05-2X/LANL2DZ level on the gas phase optimized geometries.

At the M05-2X/LANL2DZ level of theory, we did not find an energy minimum corresponding to the six-membered organorhodium intermediate in the parent system (FIG. 3). Further mechanistic exploration is needed to fully understand the subtleties of this transformation since the (E, Z)-stereochemistry of double bonds in the dienal is fully consistent with the suggested transformation of the six-membered intermediate. The stereochemistry of the two double bonds in 2a and 2b was confirmed by selective gradient-enhanced 1D NOESY (SELNOGP) and comparison to the known proton NMRs of the (E, Z) dienals 2a, 7, 8, 10 and 11. See (a) Makin, S. M.; Mikerin, I. E.; Shavrygina, O. A.; Ermakova, G. A.; Arshava, B. M. *Zh. Org. Khim.* 1984, 20, 2317. (b) Kann, N.; Rein, T.; Akermark, B.; Helquist, P. *J. Org. Chem.* 1990, 55, 5312. (c) Gravel, D.; Leboeuf, C. *Can. J. Chem.* 1982, 60, 574. (d) Taylor, R. J. K.; Hemming, K.; De Medeiros, E. F. *J. Chem. Soc., Perkin Trans.* 1 1995, 2385. (e) Bellassoued, M.; Malika, S. *Bull. Soc. Chim. Fr.,* 1997, 134, 115.

In summary, Rh-catalyzed Claisen rearrangement followed by stereoselective hydrogen transfer converts propargyl vinyl ethers into the target (E, Z)-dienals in high yields, excellent stereoselectivity and with minimal waste. The reaction tolerates steric hindrance and is compatible with substituents of different electronic demand. This atom economical method yields complex and stereochemically defined dienals in only three steps from commercially available aldehydes.

EXAMPLES

The following non-limiting examples are provided to further illustrate the present invention.

General Consideration

All commercially procured chemicals were used as received. Dichloromethane (DCM), tetrahydrofuran (THF), triethylamine ($Et_3N$), diethyl ether ($Et_2O$) were distilled from calcium hydride ($CaH_2$). Tetrahydrofuran (THF) was distilled from lithium aluminum hydride (LAH). Reagent grade solvents were used for solvent extraction and organic extracts were dried over anhydrous sodium sulfate ($Na_2SO_4$). Silica gel 60 (230-400 mesh ASTM) and neutral alumina were used for Flash Chromatography with dry hexane/ethyl acetate eluent system. $^1$H NMR and $^{13}$Cspectra were recorded on 500 MHz Bruker or 300 MHz Varian spectrometers. The proton chemical shifts (δ) are reported as parts per million relative to 2.09 quintet ppm for $CD_3C_6D_5$, 5.32 for $CD_2Cl_2$ and 7.27 for $CDCl_3$. The carbon chemical shifts (δ) were reported as the centerline of triplet at 77.0 ppm for $CDCl_3$ and quintet at 54.00 ppm for $CD_2Cl_2$. Infrared spectra were recorded on sodium chloride plates using a Perkin-Elmer FT-IR Paragon 1000 spectrometer and frequencies were reported as reciprocal of centimeters ($cm^{-1}$). Mass spectra were recorded using a Jeol JMS-600 instrument. The computations were performed using Gaussian03 on High Performance Computing facility (HPC) at Florida State University.

Computational Study

All geometries were optimized at the B3LYP/LANL2DZ and M05-2X/LANL2DZ levels which frequently performs well for the transition metal compounds (e.g. Xia, Y.; Dudnik, A. S.; Gevorgyan, V.; Li, Y. *J Am Chem Soc.* 2008, 130, 6940-6941 and Soriano, E.; Marco-Contelles, J. *Acc. Chem. Res.* 2009, 42, 1026-1036) using Gaussian 03 program (see reference). Force Field calculation indicated that optimized structures were found to be true minima with no imaginary frequency.

Gaussian 03, Revision E.01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford, Conn., 2003.

General Procedure for Vinylation of Alcohols

To a 0.1M solution of 1-phenylbut-2-yn-1-ol (1 mmol) in ethyl vinyl ether was added 0.6 mmol of mercuric acetate. The reaction mixture was refluxed at 45° C. for 12 hours before quenching with a saturated aqueous sodium carbonate solution. The organic phase was extracted using diethyl ether and dried over anhydrous potassium carbonate. The solvent was removed under vacuum and the crude vinyl ether was purified on alumina gel column using hexane as an eluent. Vinyl ether 1 was obtained in 60% yield (0.1 g).

Vinyl Ether 14

(1-(vinyloxy)but-2-yn-1-yl)benzene

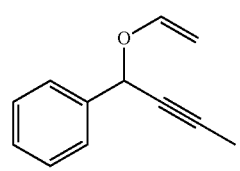

(1-(vinyloxy)but-2-yn-1-yl)benzene $^1$H NMR (500 MHz, CD$_2$Cl$_2$) δ: 7.55 (m, 2H), 7.43 (m, 3H), 6.56 (dd, J=14.1, 6.6 Hz, 1H), 5.54 (q, J=2.1 Hz, 1H), 4.51 (dd, J=14.1, 1.8 Hz, 1H), 4.21 (dd, J=6.6, 1.8 Hz, 1H), 1.97 (d, J=2.2 Hz, 3H). $^{13}$C NMR (125 MHz, CD$_2$Cl$_2$) δ: 149.6, 138.4, 128.5, 128.5, 127.2, 89.8, 84.9, 76.2, 71.1, 3.4. HRMS (EI+) Calcd. For C$_{12}$H$_{12}$O (M$^+$): 172.0888, Found: 172.0875.

Vinyl Ether 15

1-chloro-4-(1-(vinyloxy)hept-2-yn-1-yl)benzene

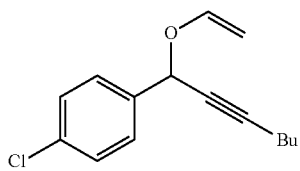

1-chloro-4-(1-(vinyloxy)hept-2-yn-1-yl)benzene $^1$H NMR (500 MHz, CD$_2$Cl$_2$) δ: 7.46 (m, 2H), 7.37 (m, 2H), 6.50 (dd, J=14.2, 6.6 Hz, 1H), 5.49 (t, J=2.0 Hz, 1H), 4.46 (dd, J=14.1, 1.9 Hz, 1H), 4.17 (dd, J=6.6, 1.9 Hz, 1H), 2.37 (s, 1H), 2.29 (td, J=7.2, 2.1 Hz, 2H), 1.52 (m, 2H), 1.42 (m, 2H), 0.91 (t, J=7.3 Hz, 3H). $^{13}$C NMR (125 MHz, CD$_2$Cl$_2$) δ: 149.4, 137.1, 134.2, 128.7, 128.6, 90.2, 89.9, 76.5, 70.3, 30.53, 21.9, 18.4, 13.3. HRMS (EI+) Calcd. For C$_{15}$H$_{17}$OCl (M$^+$): 248.0968, Found: 248.0954.

Vinyl Ether 16

4-(1-(vinyloxy)hept-2-yn-1-yl)benzonitrile

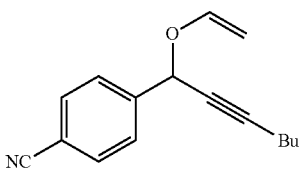

4-(1-(vinyloxy)hept-2-yn-1-yl)benzonitrile $^1$H NMR (500 MHz, CD$_2$Cl$_2$) δ: 7.72 (m, 2H), 7.67 (m, 2H), 6.55 (dd, J=14.1, 6.6 Hz, 1H), 5.60 (t, J=1.9 Hz, 1H), 4.52 (dd, J=14.1, J=2.0 Hz, 1H), 4.24 (dd, J=6.6, 2.0 Hz, 1H), 2.33 (td, J=7.2, 2.1 Hz, 2H), 1.56 (m, 2H), 1.45 (m, 2H), 0.95 (t, J=7.3 Hz, 3H). $^{13}$C NMR (125 MHz, CD$_2$Cl$_2$) δ: 149.2, 143.4, 132.3, 127.8, 118.5, 112.3, 90.6, 90.6, 30.4, 21.91, 18.3, 13.3. HRMS (EI+) Calcd. For C$_{16}$H$_{17}$ON (M$^+$): 239.1310, Found: 239.1299.

Vinyl Ether 17

(3-(vinyloxy)prop-1-yne-1,3-diyl)dibenzene

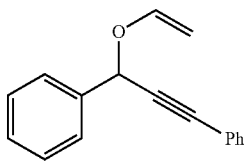

(3-(vinyloxy)prop-1-yne-1,3-diyl)dibenzene $^1$H NMR (500 MHz, CD$_2$Cl$_2$) δ: 7.64 (m, 2H), 7.53 (m, 2H), 7.49-7.36 (m, 6H), 6.63 (dd, J=14.2, 6.6 Hz, 1H), 5.80 (s, 1H), 4.59 (dd, J=14.1, 1.9 Hz, 1H), 4.27 (dd, J=6.6, 2.0 Hz, 1H). $^{13}$C NMR (125 MHz, CD$_2$Cl$_2$) δ: 149.6, 137.8, 131.7, 128.9, 128.8, 128.6, 128.4, 127.4, 122.0, 90.3, 88.1, 85.9, 71.2. HRMS (EI+) Calcd. For $C_{17}H_{14}O$ ($M^+$): 234.1045 Found: 234.1040.

Vinyl Ether 18

1,3,5-trimethyl-2-(1-(vinyloxy)but-2-yn-1-yl)benzene

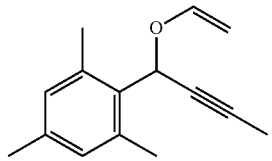

1,3,5-trimethyl-2-(1-(vinyloxy)but-2-yn-1-yl)benzene $^1$H NMR (300 MHz, $CD_2Cl_2$) δ: 6.80 (s, 2H), 6.43 (dd, J=14.1, 6.6 Hz, 1H), 5.84 (q, J=2.3 Hz, 1H), 4.43 (dd, J=14.1, 1.8 Hz, 1H), 4.11 (dd, J=6.6, 1.8 Hz, 1H), 2.46 (s, 6H), 2.30 (s, 3H), 1.90 (d, J=2.3 Hz, 3H). $^{13}$C NMR (125 MHz, $CD_2Cl_2$) δ: 149.6, 137.9, 136.5, 131.8, 129.8, 89.2, 83.4, 75.8, 67.3, 20.57, 19.9, 3.4. HRMS (EI+) Calcd. For $C_{15}H_{18}O$ ($M^+$): 214.1358 Found: 214.1364

Vinyl Ether 19

1-methyl-4-(1-(vinyloxy)but-2-yn-1-yl)benzene

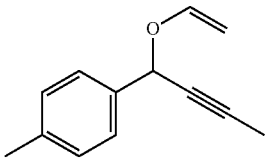

1-methyl-4-(1-(vinyloxy)but-2-yn-1-yl)benzene $^1$H NMR (500 MHz, $CD_2Cl_2$) δ: 7.42 (m, 2H), 7.25 (m, 2H), 6.53 (dd, J=13.8, 6.5 Hz, 1H), 5.49 (q, J=2.0 Hz, 1H), 4.48 (dd, J=14.0, 1.8 Hz, 1H), 4.17 (dd, J=6.6, 1.8 Hz, 1H), 2.40 (s, 3H), 1.96 (d, J=2.3 Hz, 3H). $^{13}$C NMR (125 MHz, $CD_2Cl_2$) δ: 149.6, 138.5, 135.5, 129.13, 127.2, 89.8, 84.7, 76.4, 71.0, 20.9, 3.4. HRMS (EI+) Calcd. For $C_{13}H_{14}O$ ($M^+$): 186.1045 Found: 186.1041.

Vinyl Ether 20

4-(vinyloxy)oct-2-yne

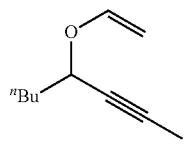

4-(vinyloxy)oct-2-yne $^1$H NMR (300 MHz, $CD_2Cl_2$) δ: 6.44 (dd, J=14.3, 7.0 Hz, 1H), 4.38 (m, 1H), 4.36 (dd, J=13.9, 1.5 Hz, 1H), 4.08 (dd, J=6.5, 1.5 Hz, 1H), 1.86 (d, 1.9 Hz, 3H), 1.73 (dtd, 8.3, 6.7, 5.6 Hz, 2H), 1.39 (m, 2H), 0.93 (t, 7.4 Hz, 3H). $^{13}$C NMR (75 MHz, $CD_2Cl_2$) δ: 146.9, 85.6, 79.1, 74.2, 66.2, 41.0, 32.3, 24.1, 19.1, 10.6. HRMS (EI+) Calcd. For $C_{10}H_{16}O$ ($M^+$): 152.1201 Found: 152.1190.

Vinyl Ether 21

5,5-dimethyl-4-(vinyloxy)hex-2-yne

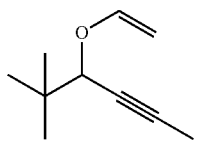

5,5-dimethyl-4-(vinyloxy)hex-2-yne $^1$H NMR (500 MHz, $CD_2Cl_2$) δ: 6.42 (dd, J=14.2, 6.6 Hz, 1H), 5.35 (q, J=2.1 Hz, 1H), 4.34 (dd, J=14.2, 1.7 Hz, 1H), 4.02 (dd, J=6.6, 2.1 Hz, 1H), 1.85 (d, J=2.1 Hz, 3H), 0.98 (s, 9H). $^{13}$C NMR (75 MHz, $CD_2Cl_2$) δ: 150.9, 88.2, 82.9, 78.1, 75.9, 35.4, 25.3, 3.2. HRMS (EI+) Calcd. for $C_{10}H_{16}O$ ($M^+$): 152.1201, Found: 152.1176.

Vinyl Ether 22

1-(1-(vinyloxy)but-2-yn-1-yl)cyclohex-1-ene

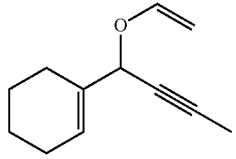

1-(1-(vinyloxy)but-2-yn-1-yl)cyclohex-1-ene $^1$H NMR (500 MHz, $CD_2Cl_2$) δ: 6.42 (dd, J=14.1, 6.6 Hz, 1H), 5.94 (m, 1H), 4.77 (m, 1H), 4.40 (dd, J=14.1, 1.7 Hz, 1H), 4.09 (dd, J=6.6, 2.0 Hz, 1H), 2.24-2.16 (m, 2H), 2.11 (m, 4H), 1.98 (m, 2H), 1.91 (d, J=2.1 Hz, 3H), 1.68 (m, 2H), 1.62 (m, 2H). $^{13}$C NMR (125 MHz, $CD_2Cl_2$) δ: 149.5, 134.9, 126.6, 89.2, 83.6, 73.9, 25.0, 24.13, 22.2, 3.3. HRMS (EI+) Calcd. For $C_{12}H_{16}O$ ($M^+$):176.1201, Found: 176.1199.

Vinyl Ether 23

2-(1-(vinyloxy)but-2-yn-1-yl)furan

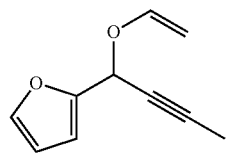

2-(1-(vinyloxy)but-2-yn-1-yl)furan $^1$H NMR (300 MHz, CD$_2$Cl$_2$) δ: 7.44 (dd, J=1.9, 0.8 Hz, 1H), 6.52 (dt, J=3.4, 0.7 Hz, 1H), 6.49 (dd, J=14.1, 6.6 Hz, 1H), 6.39 (dd, 3.5, 1.9 Hz, 1H), 5.51 (q, J=2.1 Hz, 1H), 4.45(dd, J=14.0, 1.9 Hz, 1H), 4.16 (dd, J=6.6, 1.8 Hz, 1H), 1.92 (d, J=2.3 Hz, 3H). $^{13}$C NMR (125 MHz, CD$_2$Cl$_2$) δ: 150.9, 148.9, 143.4, 110.4, 109.4, 90.2, 84.2, 73.6, 64.4, 3.3. HRMS (EI+) Calcd. For C$_{10}$H$_{10}$O$_2$ (M$^+$): 162.0681 Found: 162.0683.

Vinyl Ether 24

1,3,3-trimethyl-2-(1-(vinyloxy)but-2-yn-1-yl)cyclohex-1-ene

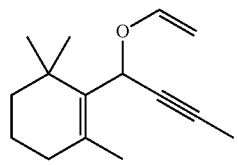

1,3,3-trimethyl-2-(1-(vinyloxy)but-2-yn-1-yl)cyclohex-1-ene $^1$H NMR (500 MHz, CD$_2$Cl$_2$) δ: 6.45 (dd, J=14.1, 6.6 Hz, 1H), 4.96 (q, J=2.3 Hz, 1H), 4.43 (dd, J=14.1, 1.5 Hz, 1H), 4.11 (dd, J=6.5, 1.6 Hz, 1H), 2.03 (t, J=6.2 Hz, 1H), 1.89 (s, 3H), 1.88 (d, J=1.5 Hz, 3H), 1.6 (m, 2H), 1.48 (m, 2H), 1.07 (s, 3H), 1.05 (s, 3H). $^{13}$C NMR (125 MHz, CD$_2$Cl$_2$) δ: 150.2, 134.9, 134.9, 88.8, 82.1, 77.6, 66.8, 39.4, 34.5, 33.5, 28.2, 27.2, 20.7, 19.2, 3.4. HRMS (EI+) Calcd. For C$_{15}$H$_{22}$O (M$^+$): 218.1671 Found: 218.1682.

Vinyl Ether 25

(3-cyclopropyl-3-(vinyloxy)prop-1-yn-1-yl)benzene

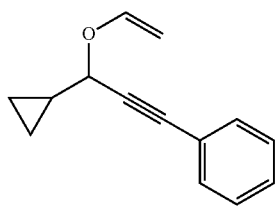

(3-cyclopropyl-3-(vinyloxy)prop-1-yn-1-yl)benzene $^1$H NMR (500 MHz, CD$_2$Cl$_2$) δ: 7.43 (m, 2H), 7.34 (m, 3H), 6.54 (dd, J=14.1, 6.6 Hz, 1H), 4.51 (d, J=6.4 Hz, 1H), 4.45 (dd, J=14.1, 1.8 Hz, 1H), 4.15 (dd, J=6.6, 1.8 Hz, 1H), 1.37 (m, 1H), 0.62 (m, 3H), 0.53 (m, 1H). $^{13}$C NMR (125 MHz, CD$_2$Cl$_2$) δ: 149.9, 131.7, 128.7, 128.3, 122.2, 89.4, 86.3, 85.1, 72.8, 14.8, 2.9, 1.8. HRMS (EI+) Calcd. For C$_{14}$H$_{14}$O (M$^+$): 198.1045 Found: 198.1046.

Vinyl Ether 26

1-(3-cyclohexyl-3-(vinyloxy)prop-1-yn-1-yl)cyclohex-1-ene

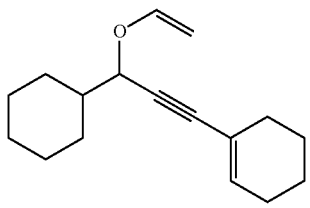

1-(3-cyclohexyl-3-(vinyloxy)prop-1-yn-1-yl)cyclohex-1-ene $^1$H NMR (500 MHz, CD$_2$Cl$_2$) δ: 6.47 (dd, J=14.1, 6.9 Hz, 1H), 6.14 (tt, J=3.5, 1.6 Hz, 1H), 4.40 (dd, J=14.3, 2.0 Hz, 1H), 4.34 (d, J=6.3 Hz, 1H), 4.10 (dd, J=6.6, 1.9 Hz, 1H), 2.17-2.09 (m, 4H), 1.88(m, 2H), 1.79 (m, 2H), 1.75-1.58 (m, 6H), 1.36-1.08 (m, 5H). $^{13}$C NMR (125 MHz, CD$_2$Cl$_2$) δ: 150.3, 135.3, 120.1, 88.8, 88.7, 83.4, 74.2, 42.6, 29.2, 28.7, 28.3, 26.4, 25.9, 25.9, 25.6, 22.3, 21.5. HRMS (EI+) Calcd. For C$_{17}$H$_{24}$O (M$^+$): 244.1827 Found: 244.1828.

General Procedure for Propargyl Claisen Rearrangement

A stock solution of [Rh(CO)$_2$Cl]$_2$ (6 mg, 0.015 mmol) was prepared in 0.3 mL toluene. To a solution of vinyl ether 1 (0.1 mmol) in 0.1M toluene under argon atmosphere was added 0.1 mL of a standard solution of [Rh(CO)$_2$Cl]$_2$. The reaction mixture was stirred for 12 to 24 hours at 50° C. Upon complete consumption of vinyl ether 1, the products were isolated using alumina column chromatography. Silica column gave mixture of EZ/EE ratios ranging from 100:3 to 100:20. The isolated products underwent slow isomerization at room temperature.

Vinyl ether 1-methoxy-4-(1-(vinyloxy)hept-2-yn-1-yl)benzene

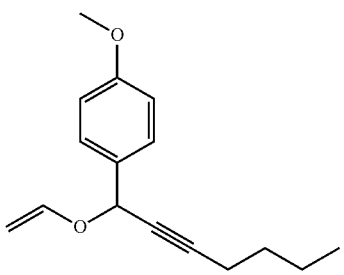

1-methoxy-4-(1-(vinyloxy)hept-2-yn-1-yl)benzene

Dienal 3

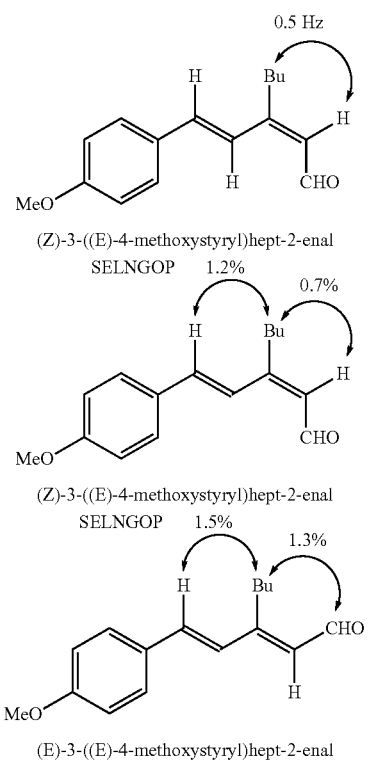

(Z)-3-((E)-4-methoxystyryl)hept-2-enal

Using the general procedure described above, 1-methoxy-4-(1-(vinyloxy)hept-2-yn-1-yl)benzene gave 85% (20.7 mg) of Dienal 3. $^1$H NMR (500 MHz, CD$_2$Cl$_2$) E, Z δ: 10.19 (d, J=7.9 Hz, 1H), 7.53 (d, J=16.1 Hz, 1H), 7.42 (m, 2H), 6.90 (d, J=16.1 Hz, 1H), 6.85(m, 2H), 5.80 (dt, J=7.9, 0.5 Hz, 1H), 3.76 (s, 3H), 2.43 (td, J=7.7, 0.6 Hz, 2H), 1.52 (m, 2H), 1.35 (m, 2H), 0.89 (t, J=7.4 Hz, 3H). E, E δ: 10.02 (d, J=8.2 Hz, 1H), 7.42 (m, 2H), 6.99 (d, J=16.2 Hz, 1H), 6.85(m, 2H), 6.64 (d, J=16.2 Hz, 1H), 5.91 (d, J=8.2 Hz, 1H), 3.75 (s, 3H), 2.43 (t, J=7.7, 2H), 1.52 (m, 2H), 1.35 (m, 2H), 0.90 (t, J=7.4 Hz, 3H).$^{13}$C NMR (125 MHz, CD$_2$Cl$_2$) δ: 190.1, 160.6, 159.2, 135.9, 128.7, 127.1, 120.5, 55.4, 34.2, 31.3, 22.6, 13.7.

Dienal 4

(Z)-3-((E)-4-chlorostyryl)hept-2-enal

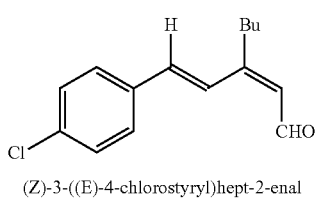

(Z)-3-((E)-4-chlorostyryl)hept-2-enal

Using the general procedure described above, 0.1 mmol (24.8 mg) vinyl ether 15 gave 91% (22.5 mg) of dienal 4. $^1$H NMR (500 MHz, CD$_2$Cl$_2$) E, Z δ: 10.28 (d, J=7.8 Hz, 1H), 7.72 (d, J=16.0 Hz, 1H), 7.52 (m, 2H), 7.41 (m, 2H), 6.99 (d, J=16.0 Hz, 1H), 5.94 (dt, J=7.7, 0.7 Hz, 1H), 2.54 (td, J=7.7, 0.8 Hz, 2H), 1.62 (m, 2H), 1.45 (tq, J=7.5, 7.4 Hz, 2H), 0.99 (t, J=7.3 Hz, 3H). $^{13}$C NMR (125 MHz, CD$_2$Cl$_2$) δ: 190.1, 158.3, 134.9, 134.7, 134.6, 129.1, 128.5, 123.5, 34.1, 31.1, 22.6, 13.6. HRMS (EI+) Calcd. For C$_{15}$H$_{17}$OCl (M$^+$): 248.0968, Found: 248.0969.

Dienal 5

4-((1E,3Z)-3-(2-oxoethylidene)hept-1-en-1-yl)benzonitrile

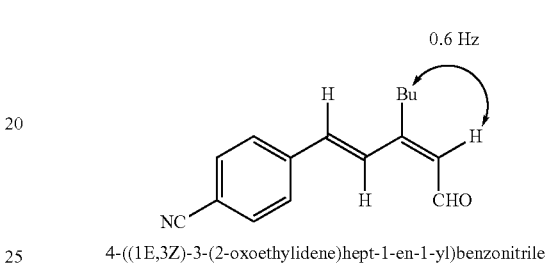

4-((1E,3Z)-3-(2-oxoethylidene)hept-1-en-1-yl)benzonitrile

Using the general procedure described above, 0.1 mmol (24.0 mg) vinyl ether 16 gave 87% (21 mg) of dienal 5. $^1$H NMR (500 MHz, CD$_2$Cl$_2$) E, Z δ: 10.27 (d, J=7.5 Hz, 1H), 7.83 (d, J=16.3 Hz, 1H), 7.72 (m, 2H), 7.66 (m, 2H), 7.02 (d, J=16.1 Hz, 1H), 6.03 (dt, J=7.6, 0.6 Hz,1H), 2.55 (td, J=7.7, 0.6 Hz, 2H), 1.62 (m, 2H), 1.46 (tq, J=7.6, 7.4 Hz, 2H), 0.99 (t, J=7.4 Hz, 3H). $^{13}$C NMR (125 MHz, CD$_2$Cl$_2$) δ: 189.9, 157.5, 140.6, 133.9, 132.6, 129.0, 127.6, 126.42, 118.6, 112.0, 30.0, 30.9, 22.6, 13.6. HRMS (EI+) Calcd. For C$_{16}$H$_{17}$ON (M$^{30}$): 239.1310, Found: 239.1315

Dienal 6

(2Z,4E)-3-methyl-5-(4-(trifluoromethyl)phenyl)penta-2,4-dienal

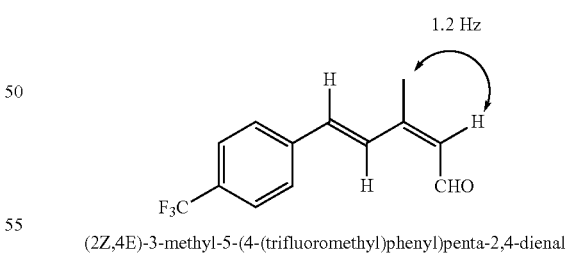

(2Z,4E)-3-methyl-5-(4-(trifluoromethyl)phenyl)penta-2,4-dienal

Using the general procedure described above, 0.1 mmol (24.0 mg) 1-(trifluoromethyl)-4-(1-(vinyloxy)but-2-yn-1-yl)benzene gave 90% (22 mg) of dienal 6. $^1$H NMR (500 MHz, CD$_2$Cl$_2$) δ: 10.29 (d, J=7.9 Hz, 1H), 7.93 (d, J=16.0 Hz, 1H), 7.65 (m, 4H), 7.03 (d, J=16.0 Hz, 1H), 5.98 (dq, J=8.5, 1.2 Hz,1H), 2.21 (d, J=1.2 Hz, 3H). $^{13}$C NMR (125 MHz, CD$_2$Cl$_2$) δ 189.6, 153.0, 139.7, 134.7, 129.6, 127.5, 125.9, 125.8, 125.7, 20.9. HRMS (EI+) Calcd. For C$_{13}$H$_{11}$F$_3$O (M$^+$):, 240.0762 Found: 240.0752.

Dienal 9

(2Z,4E)-3-methyl-5-(p-tolyl)penta-2,4-dienal

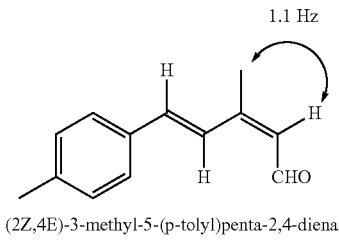

(2Z,4E)-3-methyl-5-(p-tolyl)penta-2,4-dienal

Using the general procedure described above, 0.1 mmol (19 mg) vinyl ether 19 gave 92% (17 mg) of dienal 9. $^1$H NMR (500 MHz, CD$_2$Cl$_2$) δ: 10.34 (d, J=8.2 Hz, 1H), 7.87 (d, J=16.0 Hz, 1H), 7.48 (m, 2H), 7.25 (m, 2H), 7.03 (d, J=16.0 Hz, 1H), 5.94 (dq, J=7.8, 1.1 Hz, 1H), 2.41 (s, 3H), 2.24 (d, J=1.2 Hz, 3H). $^{13}$C NMR (125 MHz, CD$_2$Cl$_2$) δ: 189.7, 154.3, 139.6, 136.6, 133.3, 129.6, 128.3, 127.3, 122.3, 21.1, 20.9. HRMS (EI+) Calcd. For C$_{13}$H$_{14}$O (M$^+$): 186.1045, Found: 186.1040.

Additional dienals were prepared according to the method of the present invention:

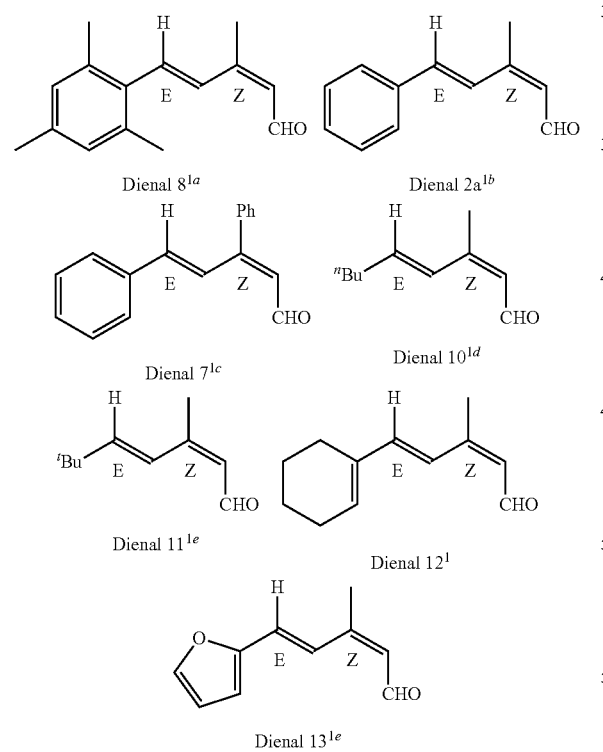

Makin, S. M.; Mikerin, I. E.; Shavrygina, O. A.; Ermakova, G. A.; Arshava, B. M. *Zh. Org. Khim.* 1984, 20, 2317. (b) Kann, N.; Rein, T.; Akermark, B.; Helquist, P. *J. Org. Chem.* 1990, 55, 5312. (c) Gravel, D.; Leboeuf, C. *Can. J. Chem.* 1982, 60, 574. (d) Taylor, R. J. K.; Hemming, K.; De Medeiros, E. F. *J. Chem. Soc., Perkin Trans.* 1 1995, 2385. (e) Bellassoued, M.; Malika, S. *Bull. Soc. Chim. Fr.,* 1997, 134, 115.

Dienal 2a (2Z,4E)-3-methyl-5-phenylpenta-2,4-dienal

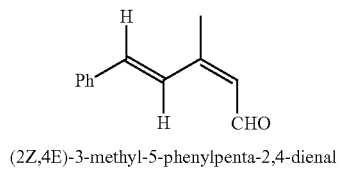

(2Z,4E)-3-methyl-5-phenylpenta-2,4-dienal

Using the general procedure described above, 0.1 mmol (17.2 mg) (1-(vinyloxy)but-2-yn-1-yl)benzene gave 85% (14.5 mg) of dienal 2a. $^1$H NMR (500 MHz, Toluene-d$_8$) E, Z δ: 10.05 (d, J=7.5 Hz, 1H), 7.20-7.03 (m, 5H), 7.53 (d, J=15.9, 1H), 6.52 (d, J=16.1 Hz, 1H), 5.71 (dq, J=7.6, 1.1 Hz, 1H), 1.63 (d, J=1.1 Hz, 3H).

Dienal 7

(2E,4E)-3,5-diphenylpenta-2,4-dienal

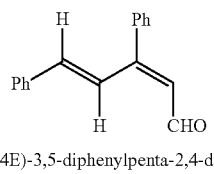

(2E,4E)-3,5-diphenylpenta-2,4-dienal

Using the general procedure described above, 0.1 mmol (24.8 mg) vinyl ether 20 gave 78% (18.5 mg) of dienal 7. $^1$H NMR (500 MHz, Toluene-d$_8$) E, Z δ: 10.06 (d, J=7.3 Hz, 1H), 7.45 (d, J=15.7, 1H), 7.15-7.01 (m, 10H), 6.55 (d, J=16.0 Hz, 1H), 6.03 (d, J=7.3, 1H). $^{13}$C NMR (125 MHz, Toluene-d$_8$) δ: 188.7, 156.4, 140.4, 139.3, 135.9, 129.7, 129.0, 128.9, 128.5, 128.4, 127.9, 127.3, 123.3.

Dienal 10

(2Z,4E)-3-methylnona-2,4-dienal

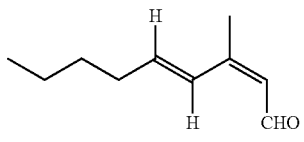

(2Z,4E)-3-methylnona-2,4-dienal

Using the general procedure described above, 0.1 mmol (24.8 mg) vinyl ether 20 gave 91% (22.5 mg) of dienal 10. $^1$H NMR (500 MHz, CDCl$_3$) E, Z δ: 10.18 (d, J=8.2 Hz, 1H), 7.08 (d, J=15.9 Hz, 1H), 6.21 (ddd, J=15.8, 8.0, 7.2 Hz, 1H), 5.82 (d, J=8.3 Hz, 1H), 2.25(m, 2H), 1.46 (m, 2H), 1.37(m, 2H), 0.94(t, J=7.5 Hz, 3H).

Dienal 11

(2Z,4E)-3,6,6-trimethylhepta-2,4-dienal

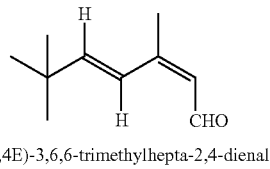

(2Z,4E)-3,6,6-trimethylhepta-2,4-dienal

Using the general procedure described above, 0.1 mmol (24.8 mg) vinyl ether 21 gave 91% (22.5 mg) of dienal 11. $^1$H NMR (500 MHz, Toluene-d$_8$) E, Z δ: 10.12 (d, J=8.0 Hz, 1H), 6.85 (d, J=15.8 Hz, 1H), 5.84 (dd, J=16.1, 0.67 Hz, 1H), 5.67 (dm, J=8 Hz, 1H), 1.58(d, J=1.2 Hz, 3H), 0.89 (s, 9H). $^{13}$C NMR (125 MHz, Toluene-d$_8$) δ: 188.2, 152.9, 149.0, 127.9, 120.7, 33.5, 28.7, 20.6.

Dienal 12

(2Z,4E)-5-(cyclohex-1-en-1-yl)-3-methylpenta-2,4-dienal

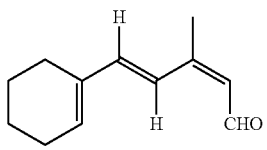

(2Z,4E)-5-(cyclohex-1-en-1-yl)-3-methylpenta-2,4-dienal

Using the general procedure described above, 0.1 mmol (24.8 mg) vinyl ether 22 gave 91% (22.5 mg) of dienal 12. $^1$H NMR (500 MHz, CDCl$_3$) E, Z δ: 10.25 (d, J=8.0 Hz, 1H), 7.19 (d, J=16.0 Hz, 1H), 6.67 (d, J=16.0 Hz, 1H), 6.11 (m, 1H), 5.88 (d, J=8 Hz, 1H), 2.27(m, 4H), 2.15 (d, J=1.1 Hz, 3H), 1.77(m, 2H), 1.69 (m, 2H). $^{13}$C NMR (125 MHz, CDCl$_3$) δ: 190.1, 155.4, 140.8, 136.3, 135.9, 127.6, 119.6, 26.5, 24.4, 22.3, 21.3.

Dienal 13

(2Z,4E)-5-(furan-2-yl)-3-methylpenta-2,4-dienal

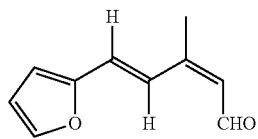

(2Z,4E)-5-(furan-2-yl)-3-methylpenta-2,4-dienal

Using the general procedure described above, 0.1 mmol (16.2 mg) vinyl ether 22 gave 95% (15.5 mg) of dienal 12. $^1$H NMR (500 MHz, CDCl$_3$) E, Z δ: 10.06 (d, J=7.5 Hz, 1H), 7.60 (d, J=15.8 Hz, 1H), 6.93 (d, J=1.6 Hz, 1H), 6.23 (d, J=15.8 Hz, 1H), 6.60 (m, 2H), 5.68 (dq, J=7.6, 1.1 Hz, 1H), 1.43 (d, J=1.1 Hz, 3H), 1.77(m, 2H), 1.69 (m, 2H). $^{13}$C NMR (125 MHz, CDCl$_3$) δ: 188.3, 152.4, 151.4, 143.4, 128.8, 121.9, 111.8, 111.5, 198.

Dienal 8

(2Z,4E)-5-(furan-2-yl)-3-methylpenta-2,4-dienal

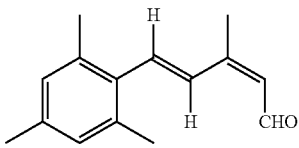

(2Z,4E)-5-mesityl-3-methylpenta-2,4-dienal

Using the general procedure described above, 0.1 mmol (21.4 mg) vinyl ether 18 gave 82% (17.5 mg) of dienal 8. $^1$H NMR (500 MHz, CDCl$_3$) E, Z δ: 10.23 (d, J=7.9 Hz, 1H), 7.36 (d, J=16.4 Hz, 1H), 7.10 (d, J=16.4 Hz, 1H), 6.96 (s, 2H), 6.00 (dq, J=8.1, 1.2 Hz, 1H), 2.37 (s, 6H), 2.34 (s, 3H), 2.28 (d, J=1.2 Hz, 3H). E, E δ: 10.02 (d, J=8.2 Hz, 1H), 7.05 (d, J=12.2 Hz, 1H), 6.89 (s, 2H), 6.83 (d, J=12.4 Hz, 1H), 5.80 (dq, J=8.3, 1.2 Hz, 1H), 2.31 (s, 3H), 2.22 (s, 6H), 1.71 (d, J=1.2 Hz, 3H).

Mercury Poisoning Experiments

The mercury poisoning experiments were performed to determine the role of nanoclusters or colloids in the proton rearrangement. The 0.1M solution of allene-aldehyde (0.1 mmols, 18.6 mg) and 5% Rh(I)-dimer (0.005 mmols, 2 mg) in toluene was monitored until the formation of 20% (E, Z)-dienal at which point the large excess of elemental mercury (4 gm) was added. The reaction was stirred vigorously for 2 hours before taking the proton NMR spectrum. Apart from reaction inhibition, we observed that the elemental mercury, instead of coalescing, stayed in the dispersed phase.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method to synthesize an (E,Z)-dienal compound having structure (V), the method comprising:
   contacting a compound having structure (IV) with a catalyst comprising Rh(I) to thereby prepare the compound having structure (V); wherein the compounds having structures (IV) and (V) have the following structures:

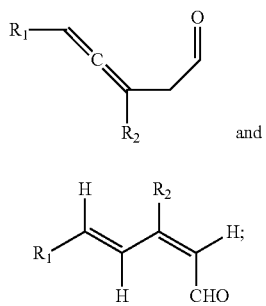

wherein

R$_1$ is selected from the group consisting of C$_{1-12}$ alkyl, C$_{2-12}$ alkenyl, C$_{2-12}$ alkynyl, C$_{3-12}$ cycloalkyl, C$_{3-12}$ cycloalkenyl, C$_{6-24}$ aryl, C$_{3-18}$ heteroaryl, amino, and C$_{1-12}$ alkylamino; and R$_2$ is selected from the group consisting of C$_{1-12}$ alkyl, C$_{2-12}$ alkenyl, C$_{2-12}$ alkynyl, C$_{3-12}$ cycloalkyl, C$_{3-12}$ cycloalkenyl, C$_{6-24}$ aryl, C$_{3-18}$ heteroaryl, amino, and C$_{1-12}$ alkylamino.

2. The method of claim 1 wherein R$_1$ comprises a C$_{6-24}$ aryl or C$_{3-18}$ heteroaryl.

3. The method of claim 1 wherein R$_1$ is substituted with a substituent selected from the group consisting of C$_{1-12}$ alkyl, C$_{2-12}$ alkenyl, C$_{2-12}$ alkynyl, C$_{3-12}$ cycloalkyl, C$_{3-12}$ cycloalkenyl, C$_{6-24}$ aryl, C$_{3-18}$ heteroaryl, halo, hydroxy, cyano, C$_{1-12}$ alkoxy, nitro, sulfinyl, sulfonyl, amino, an C$_{1-12}$ alkylamino.

4. The method of claim 1 wherein the catalyst comprising Rh(I) comprises an Rh(I)-nanocluster.

5. The method of claim 1 wherein the compound having structure (IV) is synthesized by contacting a compound having structure (III) with a catalyst comprising Rh(I):

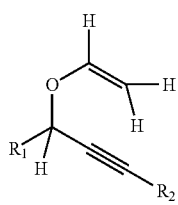

wherein

R$_1$ is selected from the group consisting of C$_{1-12}$ alkyl, C$_{2-12}$ alkenyl, C$_{2-12}$ alkynyl, C$_{3-12}$ cycloalkyl, C$_{3-12}$ cycloalkenyl, C$_{6-24}$ aryl, C$_{3-18}$ heteroaryl, amino, and C$_{1-12}$ alkylamino; and R$_2$ is selected from the group consisting of C$_{1-12}$ alkyl, C$_{2-12}$ alkenyl, C$_{2-12}$ alkynyl, C$_{3-12}$ cycloalkyl, C$_{3-12}$ cycloalkenyl, C$_{6-24}$ aryl, C$_{3-18}$ heteroaryl, amino, and C$_{1-12}$ alkylamino.

6. The method of claim 5 wherein the catalyst comprising Rh(I) comprises a homogenous catalyst.

7. The method of claim 5 wherein the compound having structure (III) is synthesized by contacting a compound having structure (I) and a compound having structure (II) according to the following sequence:

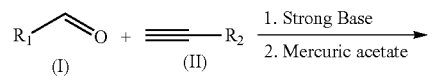

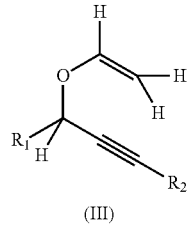

wherein R$_1$ and R$_2$ are as defined in claim 5.

8. The method of claim 5 wherein the compound having structure (III) is synthesized by contacting a compound having structure (I) and a compound having structure (II) according to the following sequence:

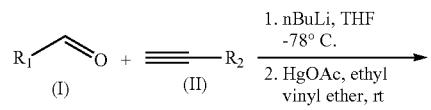

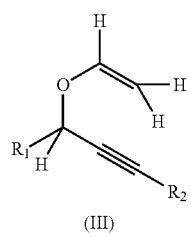

wherein R$_1$ and R$_2$ are as defined in claim 5.

* * * * *